(12) United States Patent
Malhotra et al.

(10) Patent No.: US 9,280,860 B2
(45) Date of Patent: Mar. 8, 2016

(54) FINGERPRINT SENSORS AND SYSTEMS INCORPORATING FINGERPRINT SENSORS

(71) Applicants: Arun Malhotra, Brampton (CA); Harpal Dhaliwal, Toronto (CA); Frank Gerlach, Mississauga (CA)

(72) Inventors: Arun Malhotra, Brampton (CA); Harpal Dhaliwal, Toronto (CA); Frank Gerlach, Mississauga (CA)

(73) Assignee: RISST Ltd., Toronto (CA)

( * ) Notice: Subject to any disclaimer, the term of this patent is extended or adjusted under 35 U.S.C. 154(b) by 318 days.

(21) Appl. No.: 13/743,624

(22) Filed: Jan. 17, 2013

(65) Prior Publication Data

US 2013/0234825 A1 Sep. 12, 2013

Related U.S. Application Data

(63) Continuation of application No. PCT/CA2011/000819, filed on Jul. 19, 2011.

(60) Provisional application No. 61/365,511, filed on Jul. 19, 2010.

(51) Int. Cl.
*G07C 9/00* (2006.01)
*A61B 5/117* (2006.01)
*G06K 9/00* (2006.01)

(52) U.S. Cl.
CPC .......... *G07C 9/00158* (2013.01); *A61B 5/1172* (2013.01); *G06K 9/00006* (2013.01); *G07C 9/00087* (2013.01)

(58) Field of Classification Search
CPC ........... G07C 9/00158; G07C 9/00087; G06K 9/000006; A61B 5/1172
USPC ................................................ 340/5.81–5.83
See application file for complete search history.

(56) References Cited

U.S. PATENT DOCUMENTS

| | | | |
|---|---|---|---|
| 4,394,773 A | 7/1983 | Ruell | |
| 5,933,515 A | 8/1999 | Pu et al. | |
| 5,953,441 A | 9/1999 | Setlak | |
| 5,963,679 A * | 10/1999 | Setlak | 382/312 |
| 6,346,739 B1 * | 2/2002 | Lepert et al. | 257/532 |
| 6,512,381 B2 * | 1/2003 | Kramer | 324/658 |
| 6,757,410 B1 | 6/2004 | Nakashima | |
| 6,810,480 B1 * | 10/2004 | Parker et al. | 713/186 |
| 7,006,078 B2 * | 2/2006 | Kim | 345/173 |
| 7,013,031 B2 * | 3/2006 | Kim et al. | 382/124 |
| 7,067,962 B2 * | 6/2006 | Scott | 310/334 |
| 7,239,153 B2 | 7/2007 | Nysaether | |
| 7,835,553 B2 * | 11/2010 | Miyasaka | 382/124 |

(Continued)

OTHER PUBLICATIONS

International Search Report issued in PCT/CA2011/000819 (date of mailing Nov. 2, 2011).

(Continued)

*Primary Examiner* — Hai Phan
*Assistant Examiner* — Son M Tang
(74) *Attorney, Agent, or Firm* — Bereskin & Parr LLP/S.E.N.C.R.L.,s.r.l.

(57) ABSTRACT

Various embodiments of access control systems and fingerprint sensing systems are disclosed. One or more fingerprints of an authorized person are recorded in a fingerprint database together with a sequence of angular positions. The authorized person may subsequently gain access to a secured item by scanning the authorized person's finger or fingers in accordance with the sequence of angular positions. Various embodiments of fingerprint sensors for determining the angular position of a finger on the sensor are also disclosed.

33 Claims, 18 Drawing Sheets

(56) References Cited

U.S. PATENT DOCUMENTS

| | | | | |
|---|---|---|---|---|
| 8,051,476 B2* | 11/2011 | McArdle | | 726/17 |
| 8,320,638 B2* | 11/2012 | Pitt et al. | | 382/115 |
| 2004/0028261 A1* | 2/2004 | Tufvesson | | 382/124 |
| 2005/0041841 A1* | 2/2005 | Yoo et al. | | 382/124 |
| 2005/0129290 A1* | 6/2005 | Lo et al. | | 382/124 |
| 2009/0097720 A1 | 4/2009 | Roy et al. | | |
| 2010/0158327 A1* | 6/2010 | Kangas et al. | | 382/124 |

OTHER PUBLICATIONS

Written Opinion issued in PCT/CA2011/000819 (date of mailing Nov. 2, 2011).

* cited by examiner

FINGERPRINT SENSORS AND SYSTEMS INCORPORATING FINGERPRINT SENSORS

FIELD

The described embodiments relate to fingerprint sensors and to systems that incorporate fingerprint sensors.

BACKGROUND

Various security systems require the use of biometric systems to provide access for an authorized person to a product, location or service or to authenticate the presence of an authorized person at a particular location. For example, security locks may be configured to be released when an approved fingerprint is scanned at a fingerprint scanner. Some personnel tracking system require an authorized person to scan an approved fingerprint at a fingerprint scanner to prove that the authorized person is present at the location of the fingerprint scanner. The use of biometric such as a fingerprint to identify an authorized person has the advantage that the authorized person is positively identified. Other persons typically do not share the same biometric. Depending on the nature of the scanner, it may be possible for an unauthorized person to present an approved fingerprint in the form of a two or three dimensional copy such as an image or model or as part of a severed finger. Fingerprints are essentially permanent characteristics of a person. An unauthorized person who is able to present an authorized fingerprint can only be stopped from gaining access by de-authorizing the fingerprint.

Some security systems avoid the problem of using an immutable biometric of an authorized person by using a passcode such as a password or a sequence of gestures. The passcode may be issued for use by an authorized person, and may be cancelled or replaced as needed when a person is no longer authorized or as a new passcode is needed. In addition a passcode has the advantage that it can be memorized or otherwise recorded by a person but is not an immutable physical characteristic. A passcode can be changed as needed. However, passcodes suffer from the problem that they can be stolen using keyloggers, cameras or guessed by unauthorized persons. Passcodes can also be disclosed to an unauthorized person through carelessness or inadvertence.

SUMMARY

It is desirable to provide security systems and methods that have both the positive identification provided by the use of a biometric and the flexibility provided by the use of a passcode. The embodiments described below provide such systems and methods, thereby allowing positive identification of an unauthorized person while also requiring the authorized person to input or enter a passcode to gain access or to authenticate the presence of an unauthorized person at a location.

In a first aspect, some embodiments provide a fingerprint sensing system comprising: fingerprint sensor having: sensor die; a die connection layer coupled to the sensor die; and two or more drive signal injection points, wherein each signal injection point is electrically isolated from the sensor die; and a controller coupled to the drive signal injection points for injecting a drive signal into each drive signal injection point and to the die connection layer for receiving a fingerprint signal from the sensor die, wherein the fingerprint signal corresponds to less than all of the drive signals.

In some embodiments, the fingerprint sensor includes a bezel and wherein the drive signal injection points are positioned on the bezel.

In some embodiments, the signal injection points are formed in a continuous bezel at least partially surrounding the sensor, such that a finger may be positioned in contact with the sensor die and one of the signal injection points to couple a drive signal from the signal injection point to the sensor die.

In some embodiments, the bezel is grounded between adjacent signal injection points.

In some embodiments, the system further includes a segmented bezel having bezel segments that are electrically isolated from one another, wherein each bezel segment includes a signal injection point and when a finger is positioned in contact with both the sensor die and one of the bezel segments, a drive signal is coupled from the bezel segment to the sensor die.

In some embodiments, the controller is configured to determine an angle corresponding to the fingerprint signal.

In some embodiments, the angle corresponds to the position of one or more drive signal injection points.

In some embodiments, the fingerprint signal corresponds to one of the drive signals.

In some embodiments, the bezel includes finger positioning guides corresponding to the position of the drive signal injection points.

In another aspect, some embodiments provide a method of authorizing an action, the method comprising: providing a plurality of authentication sequences, wherein each authentication sequence comprises: an authorized person identifier; two or more sequential angular positions; providing a plurality of authorized person records, wherein each person record includes: a person record identifier; and a fingerprint record; two or more sequential angular positions; sensing a fingerprint; identifying a person by comparing the sensed fingerprint to fingerprint records in one or more person records; determining an angular fingerprint position contemporaneously with the sensing the fingerprint; repeating the steps of sensing, identifying and determining at least once and, for each iteration, recording the identified person and the angular position if the identified person for each iteration, and if identified person in each iteration corresponds to an authorized person and recorded sequence of angular positions corresponds to the same authorized person, then authorizing the action.

In various embodiments, fingerprint sensing systems and access control systems may operate in a low power normal operation modes. In some embodiments, the systems may be combined with other access control and authentication systems, such as magnetic or RFID cards and tags.

In another aspect, some embodiments provide a method of operating an access control system, the method comprising: recording fingerprint data corresponding to one or more fingers of a particular authorized person; recording a sequence of finger positions for the particular authorized person; receiving a series of fingerprint signals from a fingerprint sensor; determining a sequence of angular positions corresponding to sequential fingerprint signals in the series; determining if each of the fingerprint signals corresponds to the recorded fingerprint data; determining if the sequence of angular positions corresponds to the recorded sequence of finger positions; and if the fingerprint signals corresponds to the recorded fingerprint data and the sequence of angular positions corresponds to the recorded sequence of fingerprint positions, then providing an authorization signal.

In some embodiments, the authorization signal includes an identification of the authorized person.

In some embodiments, the sequence of finger positions is specified by the authorized person.

In some embodiments, the fingerprint data corresponds to one or more fingers of the authorized person positioned in multiple angular positions on a fingerprint sensor.

In some embodiments, the fingerprint data corresponds to one or more fingerprints of the authorized person in a standard orientation.

In some embodiments, the fingerprint data and the sequence of finger positions of the particular authorized person are recorded in an authorized person record in a fingerprint database that contains authorized person records for a plurality of authorized persons.

In some embodiments, the method includes requiring the particular authorized person to identify himself or herself prior to providing the authorization signal.

In another aspect, some embodiments provide a method of operating an access control system, the method comprising: recording fingerprint data corresponding to one or more fingers of a particular authorized person rotated at a variety of angles on a fingerprint sensor; recording a sequence of angular finger positions for the particular authorized person; receiving a series of fingerprint signals from a fingerprint sensor; and if each of the fingerprint signals corresponds to the recorded fingerprint data and to the sequence of angular finger positions, then providing an authorization signal.

In some embodiments, the authorization signal includes an identification of the particular authorized person.

In some embodiments, the sequence of finger positions is specified by the particular authorized person.

In some embodiments, the fingerprint data and the sequence of finger positions of the particular authorized person are recorded in an authorized person record in a fingerprint database that contains authorized person records for a plurality of authorized persons.

In some embodiments, the method includes requiring the particular authorized person to identify himself or herself prior to providing the authorization signal.

In another aspect, some embodiments provide a method of operating a fingerprint sensing system, the method comprising: providing a fingerprint sensor having a sensor die and a bezel, wherein the bezel has a plurality of drive signal injection points; injecting a drive signal into each of the drive signal injection points;

receiving a fingerprint signal from the fingerprint sensor, wherein the fingerprint signal corresponds to at least one of the drive signals; and determining the drive signal or drive signals to which the fingerprint signal corresponds.

In some embodiments, the drive signal injection points are spaced about the bezel.

In some embodiments, the drive signal injection points are located at various angular positions about the bezel.

In some embodiments, the method includes varying the magnitude of some or all of the drive signals to control a signal-to-noise ratio of the fingerprint signal.

In some embodiments, the method includes varying the magnitude of some or all of the drive signals to control lines and gaps in a fingerprint image obtained from the fingerprint signal.

In some embodiments, the method includes determining an angular orientation of a finger positioned on the fingerprint sensor.

In some embodiments, the method includes repeating the steps of receiving a fingerprint signal and determining the drive signal or drive signals to which the fingerprint signal corresponds and further including recording a sequence of drive signals corresponding to the received fingerprint signals.

In some embodiments, the drive signals are different from one another.

In some embodiments, the drive signals have temporally distinct active and inactive phases.

In some embodiments, the drive signals have different shapes, each of which is distinguishable from the other drive signals.

In another aspect, some embodiments provide a fingerprint sensing system comprising: fingerprint sensor including: a bezel having a plurality of signal injection points; a sensor die electrically insulated from the bezel; and a controller coupled to the fingerprint sensor to receive a fingerprint signal, wherein the controller includes: a plurality of drive signal blocks, wherein each drive signal block is coupled to a corresponding signal injection point to inject a drive signal into the corresponding signal injection point.

In some embodiments, the bezel and sensor die are positioned to allow each of the drive signals to be coupled to the sensor die by a finger in contact with the corresponding drive signal injection point and the sensor die.

In some embodiments, each drive signal is unique.

In some embodiments, each of the drive signals has an active phase and an inactive phase, wherein only one drive signals is in an active phase at any particular time.

In some embodiments, the controller and the fingerprint sensor are coupled through a wired communication link.

In some embodiments, the controller and the fingerprint sensor are coupled through a wireless communication link.

In some embodiments, the bezel is formed of a conductive material.

In some embodiments, the bezel is formed of a conductive material selected from the group consisting of conductive plastics and metal.

In some embodiments, the bezel is a continuous bezel.

In some embodiments, the bezel is a continuous bezel and wherein the bezel is grounded between at least some adjacent signal injection points.

In some embodiments, the bezel is a segmented bezel formed of a plurality of bezel segments and wherein at least some of the signal injection points are provided on different bezel segments.

In some embodiments, the bezel is a segmented bezel formed of a plurality of bezel segments and wherein at least some of the signal injection points are provided on different bezel segments.

In some embodiments, the bezel is grounded between at least some adjacent signal injection points.

In some embodiments, the bezel is a segmented bezel and wherein each signal injection point is provided on a different bezel segment.

In another aspect, some embodiments provide an access control system comprising: a fingerprint sensor; a controller coupled to the fingerprint sensor; and a fingerprint database coupled to the controller, wherein the fingerprint database includes a plurality of authorized person records, each of the authorized person records containing fingerprint data corresponding to an authorized person and an authorized angle sequence.

In some embodiments the fingerprint data includes data corresponding to one or more of the particular authorized person's fingerprints positioned at a plurality of angular positions on the fingerprint sensor.

These and other aspects of the invention as discussed below.

BRIEF DESCRIPTION OF THE DRAWINGS

A preferred embodiment of the present invention will now be described in detail with reference to the drawings, in which.

Figure 1:
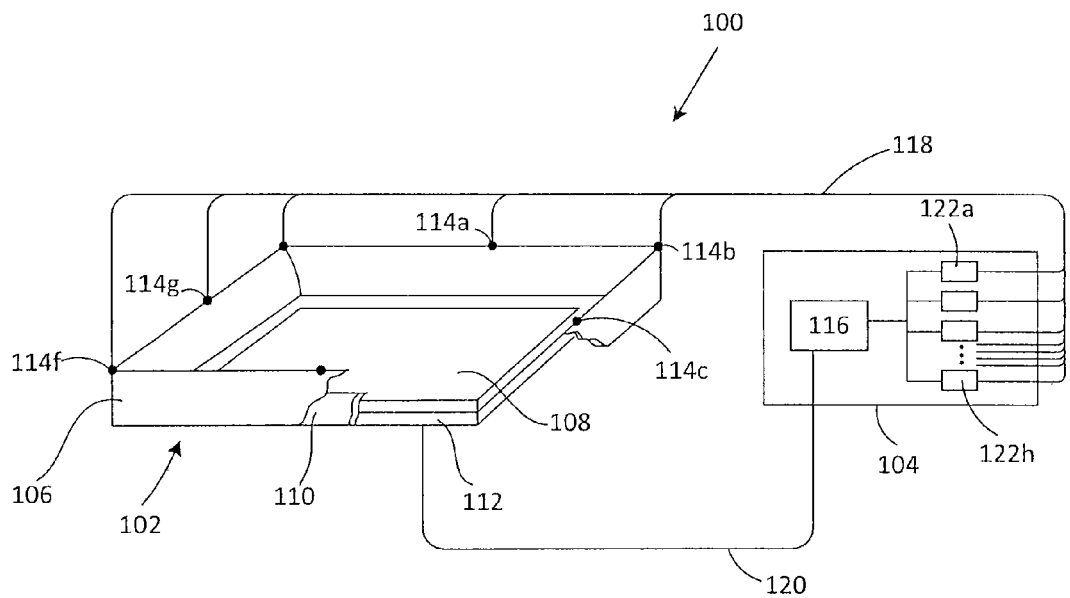
FIG. 1 is a partial cutaway drawing of a fingerprint sensing system.

It will be understood that the drawings are exemplary only. All reference to the drawings is made for the purpose of illustration only and is not intended to limit the scope of the embodiments described herein below in any way. For convenience, reference numerals may also be repeated (with or without an offset) throughout the figures to indicate analogous components or features.

DESCRIPTION OF EXEMPLARY EMBODIMENTS

Figure 2:
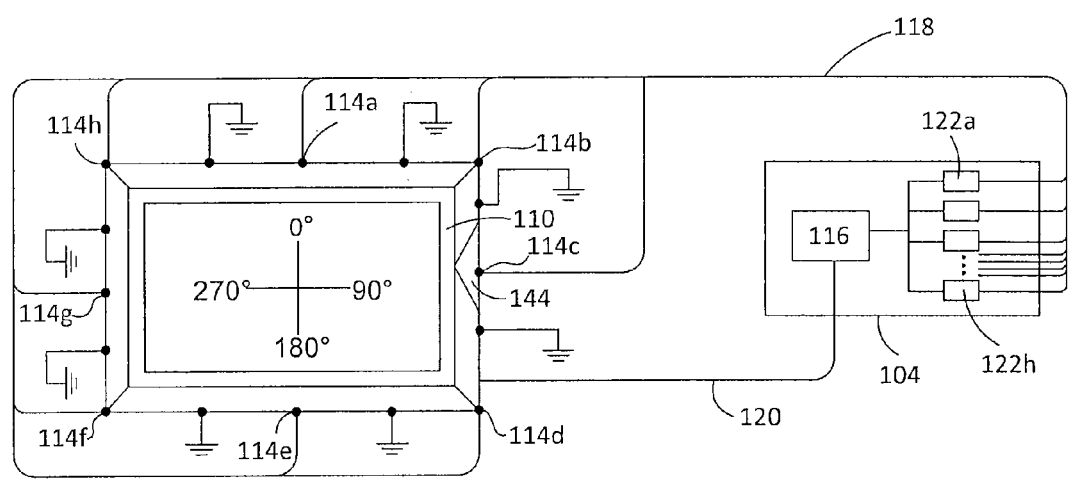
FIG. 2 is another view of the system of FIG. 1.
Figure 2:
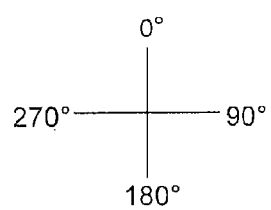

Reference is first made to FIGS. 1 and 2, which illustrate a first embodiment of a fingerprint sensing system 100. System 100 includes a fingerprint sensor 102 and a controller 104.

Fingerprint sensor 102 includes a bezel 106, a sensor die 108, insulation 110 and a die connection layer 112. Bezel 106 is a continuous resistive ring having a plurality of signal injection points 114a-114h. The bezel 106 is grounded between each pair of adjacent signal injection points 114. Each injection point 114 has a corresponding drive signal connection 116a-116h. In various embodiments, the bezel may be formed of various conductive materials, including conductive plastics, metal and other materials.

Controller 104 is coupled to sensor 102 through a cable 118 and cable 120. Controller 104 includes a processor 116, a plurality of drive signal blocks 122a-122h and a signal sensor block 124. Cable 18 may be a multi-conductor cable or a parallel or serial communications cable or any other type of communication link. In some embodiments, the controller and sensor may be coupled through a wireless communication link. Processor 116 may be any type of programmable processing device including a programmed computer, a microcontroller, a logic array such as a programmed gate array or field programmable gate array, a programmable logic controller, a central processing unit, a digital signal processor, a general purpose computer, a microprocessor or any hardware or software device capable of controlling system 100 to operate as described herein.

Each drive signal block 122 is coupled to a corresponding signal injection point 114 through cable 118. Die connection layer 112 is coupled to signal sensor block 124 through cable 120.

Figure 3:
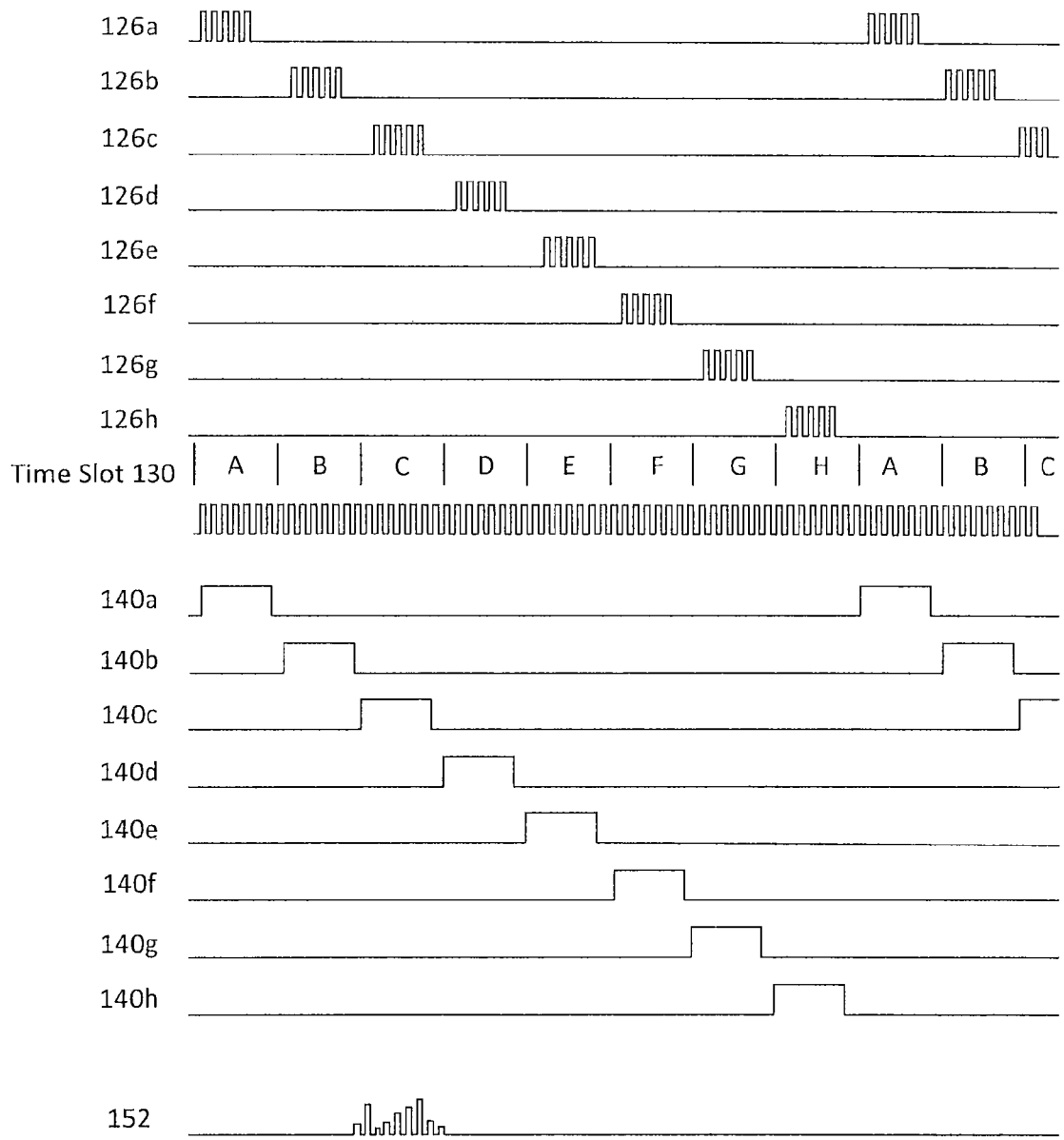
FIG. 3 is a timing diagram illustrating some signals in the system of FIG. 1.

Referring also to FIG. 3, each drive signal block 122a-122h generates a drive signal 126a-126h that is injected into the corresponding signal injection point 114a-114h. Each drive signal 126a-126h is unique, in that it is distinguishable from each other drive signal injected into the fingerprint sensor 102. In this embodiment, each drive signal 126 has an active phase 128 and an inactive phase 129. Each drive signal is synchronized to a common time base so that no more than one of the signals is active at any particular time. In this embodiment, each drive signal 126a-126h has a corresponding time slot 130a-130h during which it has its respective active phase. During the time slots 130 allocated to other drive signals 126, each drive signal is in its inactive phase. In this embodiment, during the inactive phase, each signal has a magnitude of 0. During the active phase, each drive signal is a 1 MHz square wave with a 1 volt peak to peak magnitude.

Figure 4:
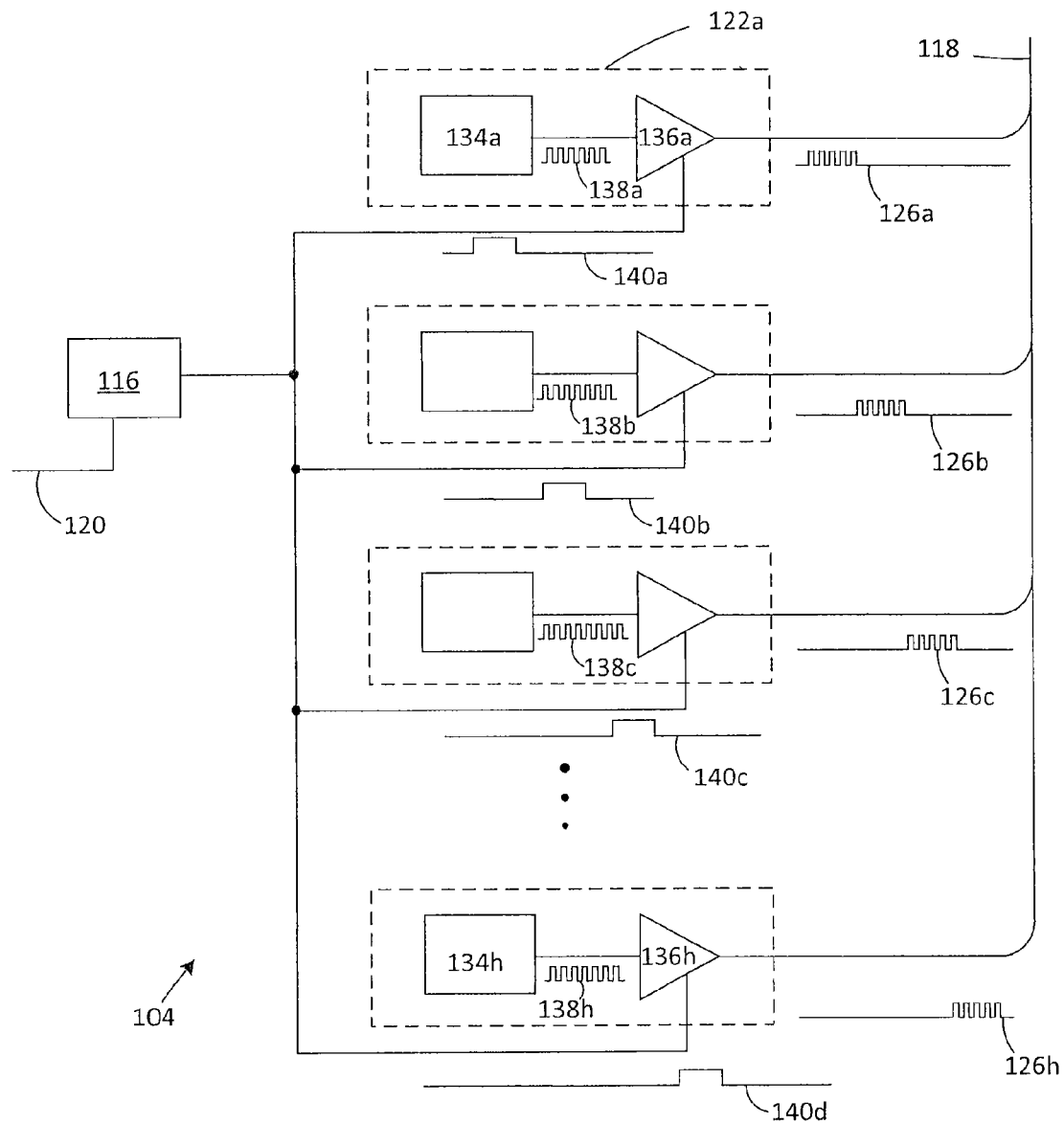
FIG. 4 is a block diagram of a controller of the system of FIG. 1.

Referring to FIG. 4, each drive signal block 122a-122h includes a signal generation block 134a-134h and an amplifier 136a-136h. Each signal generation block 134a-134h generates a drive signal waveform 138a-138h, which in this embodiment is a square wave. Each amplifier 136a-136h is coupled to processor 116, which generates a gain control signal 140a-140h for to each signal generation block 122a-122h. Each amplifier 136 generates the corresponding drive signal 126 by selectively amplifying the corresponding square wave 138 in response to the corresponding gain control signal 140.

Referring to FIG. 3, gain control signal 140a has a magnitude greater than zero during time slot 130a and a magnitude of zero during time slots 130b-130h. When the gain control signal 140a is 0, the corresponding drive signal 126a, amplifier 136a generates drive signal 126a with a magnitude of 0. When gain control signal 140a is non-zero, amplifier 136 generates drive signal 126a such that it is an amplified version of square wave 138a. The amplification factor is determined by the magnitude of the gain control signal 140a, allowing the processor 116 to control the magnitude of the drive signal 126a. Each of the drive signals 126a-126h is generated in a corresponding manner such that the magnitude and timing of each of the drive signals is controlled by processor 116.

In some embodiments, the gain control signals may be digital signals with high and low values. When a gain control signal has a high value, the corresponding drive signal waveform is output as a drive signal. When the gain control signal has a low value, the drive signal has a zero output. In embodiments where the drive signals are not distinguished based on time slices or time slots, the gain control signal may provide an amplification value. In embodiments where the drive signals are not distinguished based on time slices or time slots and it is not desired to control the magnitude of the drive signal, the drive signal waveform generated by the signal generation block may be output as a drive signal.

Referring again to FIGS. 1 and 2, each drive signal 126 is injected into the corresponding signal injection point 114 through cable 118. Bezel 106 is conductive and the injected drive signals propagate into and through the bezel 106. Bezel 106 is grounded between signal injection points limiting the portion of the bezel 106 into which a drive signal injected at a particular signal injection point 114 propagates. For example, drive signal 126c injected at signal injection point 114c may propagate primarily through region 144. Similarly, drive signal injected at other signal injection points 114 propagate through regions of the bezel adjacent the signal injection points.

Figure 5:
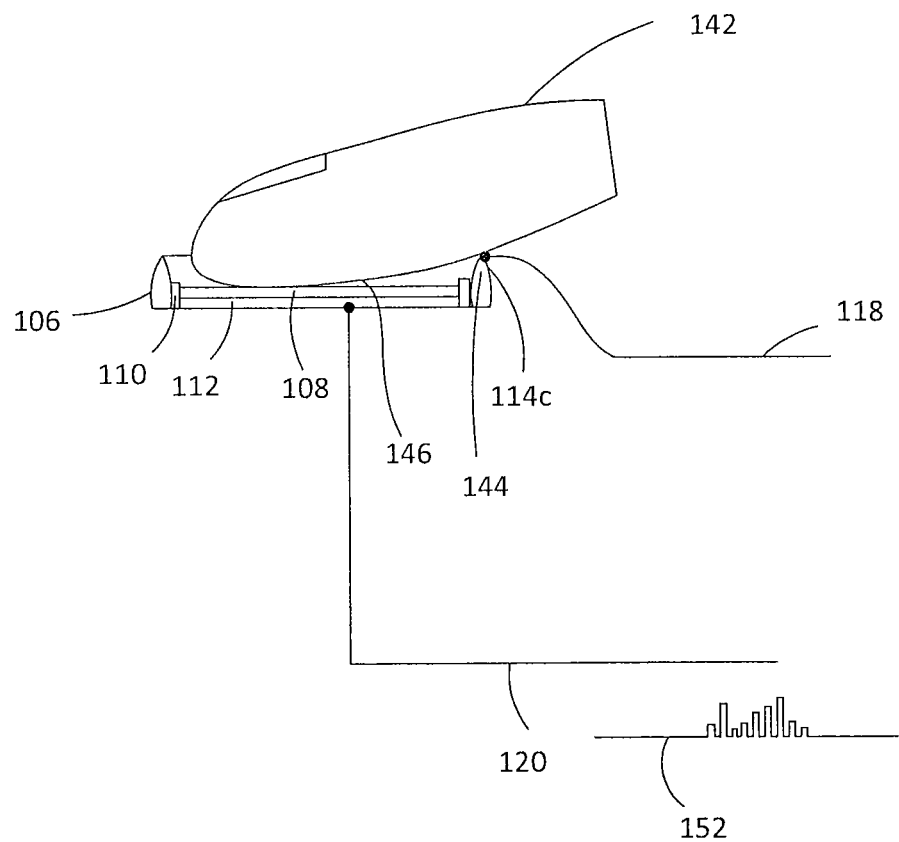
FIG. 5 illustrates a fingerprint sensor of the system of FIG. 1 in use.
Figure 5A:
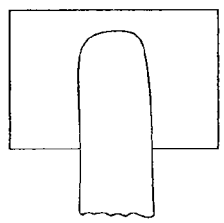
FIGS. 5a-5h illustrate a finger positioned on a fingerprint sensor at various angular positions.
Figure 5B:
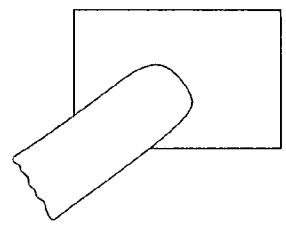
Figure 5C:
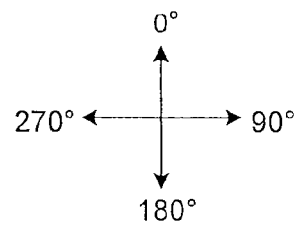
Figure 5C:
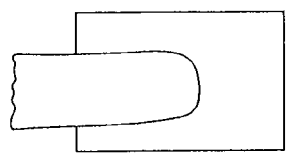
Figure 5D:
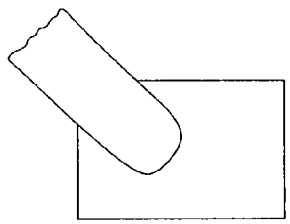
Figure 5E:
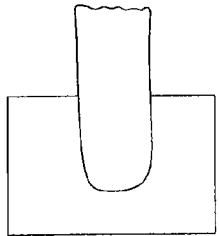
Figure 5F:
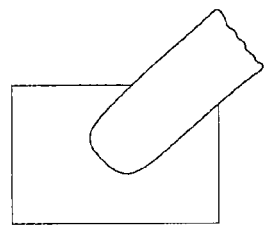
Figure 5G:
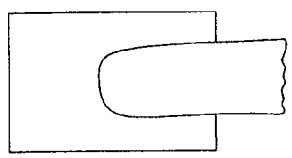
Figure 5H:
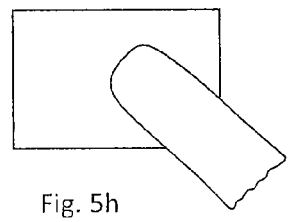

Reference is next made to FIG. 5, which illustrates system 100 in use. A person's finger 142 is illustrated on the fingerprint sensor 102. Finger 142 is in contact with bezel 106 in region 144, through which drive signal 126c propagates. Finger 142 is also in contact with the sensor die 108, such that a fingerprint 146 on the finger 142 is pressed against the sensor die.

Finger 142 is conductive. Drive signal 126c is coupled into finger 142 from region 144 of bezel 106. The drive signal 126c is then coupled from finger 142 to sensor die 108. Insulation 110 is positioned between bezel 106 and sensor die 108 to prevent drive signals from being directly from the bezel to the sensor die. A dermal layer of the finger 142 is charged by the drive signal 126c coupled into it (while the drive signal is at a non-zero level).

Sensor die 108 is a capacitive sensing element with a two-dimensional array of sensing elements 150 (FIG. 1). The conductive dermal layer of the finger 142 and the sensor die form the plates of an effective capacitor, which is charged by the drive signal coupled into the finger. Between the dermal layer and the sensor die is a non-conductive epidermal layer of skin on the finger 142, in which ridges and valleys of the fingerprint 146 are formed. The epidermal layer and air within the valleys of the fingerprint provide a dielectric layer for the effective capacitor. Each sensing element 150 senses a charge from the adjacent portion of the finger 142 and provides a charge intensity signal corresponding to the intensity of the charge. The sensed charge at different sensor elements differs depending on the presence of a ridge in the fingerprint or air in a valley in the fingerprint. The die connection layer receives the charge intensity signals from each sensor element and transmits a fingerprint signal 152 to the processor 116. Typically, die connection layer is coupled to each sensor element 150 and includes a processing element to generate fingerprint signal 152. The operation of the sensor die and die connection layer are not described in detail here as a skilled person will understand the operation of a capacitance based fingerprint sensing element. Processor 116 receives the fingerprint signal and forms a fingerprint image 154 corresponding to the fingerprint 146.

The fingerprint signal 152 corresponds to both the fingerprint 146 and to the particular drive signal 126 coupled from the bezel 106 into the sensor die 108. In system 100, the charging signals 126a-126h have temporally spaced active phases. Finger 142 will be charged only when it is in contact with a region of the bezel 106 in which a non-zero driving signal is injected (or propagated). As a result, fingerprint signal 152 will contain information about fingerprint 146 only while drive signal 126c is in its active phase. At other times, drive signal 126c is in its inactive phase and does not charge finger 142. Although the other drive signals 126a-126b and 126d-126h also have active phases and are injected in the bezel, these drive signals are essentially prevented from being coupled into finger 142 by the ground connections on bezel 106 between their respective signal injection points 114. As a result, fingerprint signal 152 will contain data corresponding to fingerprint 146 during the active phase of drive signal 146c. At other times, fingerprint signal 152 will not typically contain data corresponding to a fingerprint.

Processor 116 controls the operation of system 100 such that drive signals 126 are transmitted repetitively to the fingerprint sensor 102 and fingerprint signal 152 is transmitted repetitively to the processor 116. Typically, the active phase of each drive signal may be transmitted numerous times per second. In various embodiments, the active phase of each signal may be transmitted 10 or more times, and possibly several hundred or more times per second. During the active phase of a drive signal that is coupled to a finger 142, the fingerprint signal 152 may be analyzed to identify the presence of a finger and to obtain a fingerprint image 154.

Referring to FIGS. 2 and 3, processor 116 is able to determine which drive signal 126 that is being coupled to finger 142 based on the time at which the fingerprint signal 152 contains data corresponding to a fingerprint. Based on the coupled drive signal 126, processor 116 may determine the angular position of the finger. For example, in FIG. 5, finger 142 is at a 90 degree position.

Figure 14:
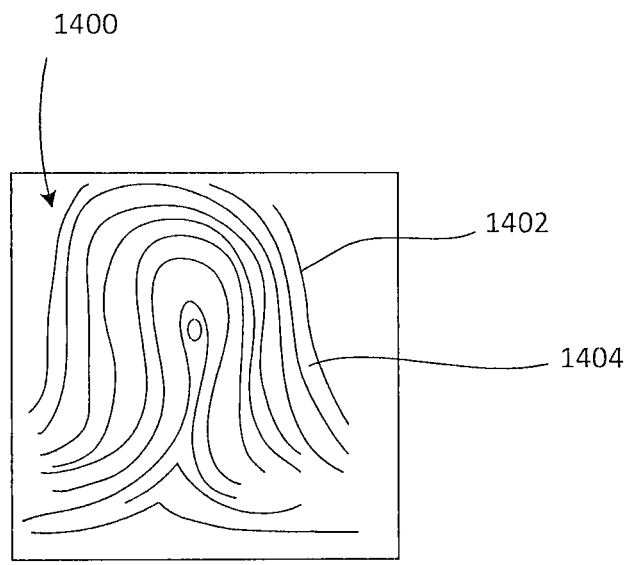
FIG. 14 illustrates a fingerprint.

Reference is made to FIG. 14, which illustrates a fingerprint 1400. Fingerprint 1400 includes varies lines 1402 and gaps 1404 that correspond to the ridges and valleys in a person's fingerprint. The lines and gaps are formed because ridges in the fingerprint couple more energy from a drive signal into sensing elements 150 of sensor die 108 than do the valleys. If the magnitude of the drive signal is too high, then the lines may be formed too wide, with small or no gaps between them. If the magnitude of the drive signal is too low, then the lines 1402 may be faint or missing. In some embodiments, the processor 116 may vary the magnitude of some or all of the gain control signals in response to the fingerprint signal 152. The processor may vary gain control signals 140 to control the signal-to-noise ratio or to control the density of lines 1402 and gaps 1404 in the fingerprint. In other embodiments, the processor may be able to control the drive signal block to vary the frequency or shape of some or all of the drive signals to improve a fingerprint image.

Referring to FIGS. 5a-5h, finger 142 is illustrated with the tip of the finger pointed in various directions. The drive signal coupled into finger 142 in each position is as follows:

| Figure | Finger positions | Drive Signal |
|---|---|---|
| 5a | 0 degrees | 126a |
| 5b | 45 degrees | 126b |
| 5c | 90 degrees | 126c |
| 5d | 135 degrees | 126d |
| 5e | 180 degrees | 126e |
| 5f | 225 degrees | 126f |
| 5g | 270 degrees | 126g |
| 5h | 315 degrees | 126h |

Figure 6:
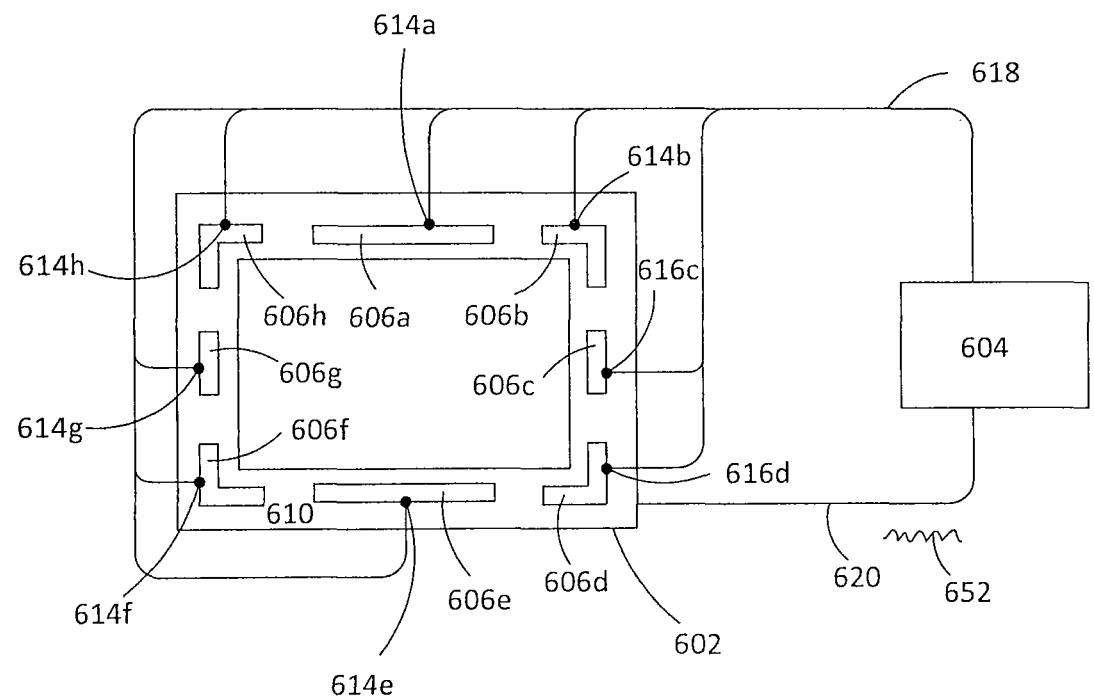
FIG. 6 is a block diagram of another fingerprint sensing system.

Reference is next made to FIG. 6, which illustrates another fingerprint sensing system 600. System 600 is similar to system 100 and corresponding components are identified by similar reference numerals.

The fingerprint sensor 602 of system 600 has a segmented bezel comprised of bezel segments 606a-606h, rather than the continuous bezel 106 of system 100 (FIG. 1). Each bezel segment 606 has a signal injection point 614a-614h, which is coupled to controller 604 to receive a drive signal 626a-626h (not shown). System 600 operates in a similar manner to system 100. Controller 604 generates and injects drive signals 626a-626h into each bezel segment. Like system 100, each of the drive signals has an active phase and an inactive phase such that the active phase of each drive signal occurs during the inactive phase of each of the other signals. The bezel segments 606 are electrically insulated from one another by insulator 610 so that the drive signal 626 injected into each bezel segment does not propagate into any other bezel segment through the insulator 610. When a finger is placed on the fingerprint sensor 602 touching one of the bezel segments 606 and the sensor die 608, the drive signal 626 coupled to that bezel segment 606 is coupled into the finger and then into the sensor die 608. The die connection layer 612 produces a fingerprint signal 652 that is transmitted to the processor 616 through cable 620. As described above in relation to system 100 (FIG. 1), processor 616 may be configured to determine the angular position of the finger by determining which drive signal 626 was coupled to the sensor die 608.

Referring briefly to FIG. 1, in system 100, it may be possible for a drive signal 126 to propagate beyond the immediate region of its corresponding signal injection point 114, depending on the ground connections between signal injection points and the conductivity of the bezel 106. The bezel segments 606 of system 100 provide a greater degree of isolation between drive signals since the bezel segments are isolated from one another.

In systems 100 and 600, the active phases of each of the drive signals are spaced in time so that the specific drive signal coupled to the respective sensor dies may be determined based on the time slot in which the fingerprint signal contains fingerprint data.

Figure 7:
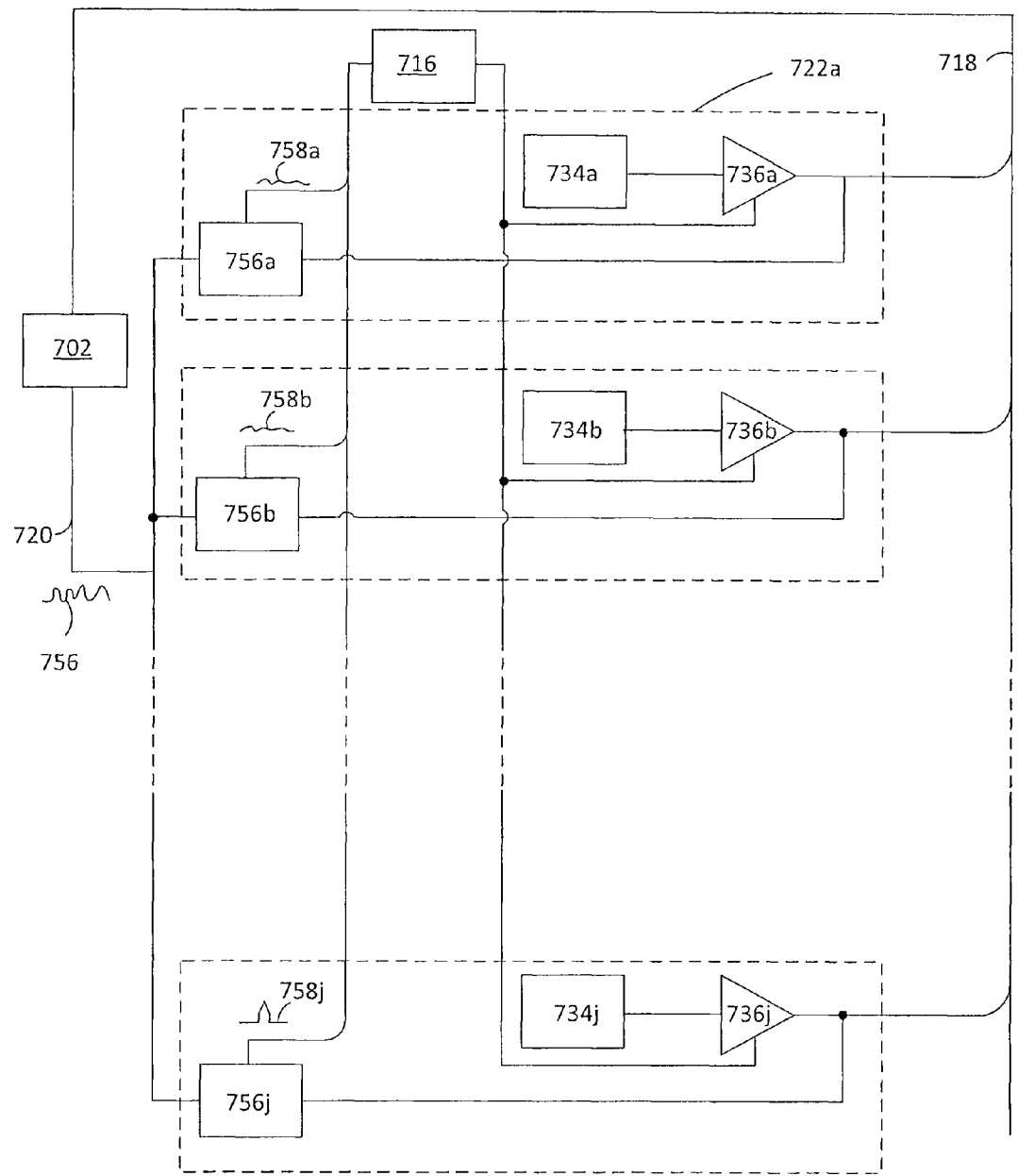
FIG. 7 is a block diagram of another fingerprint sensing system.
Figure 8:
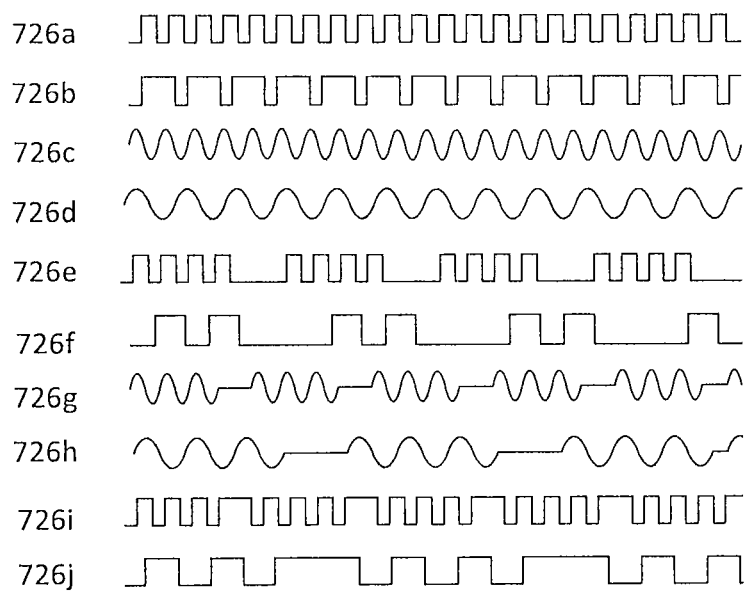
FIG. 8 is a timing diagram illustrating some signals in the system of FIG. 7.

Reference is next made to FIG. 7, which illustrates a fingerprint sensing system 700. System 700 is similar to system 600 and corresponding components are identified by similar reference numerals. In system 700, the drive signals 726a-726h are distinguishable by their distinct shapes, but do not have temporally distinct active and inactive phases. Referring to FIG. 8, the drive signals 726 have different shapes, each of which is distinguishable from the other drive signals. Each drive signal 726a-726h is injected into the corresponding bezel segment 706a-706h during operation of system 700. A finger positioned in contact with one of the bezel segments 706 and the sensor die 708 will couple the corresponding drive signal 726 from the bezel segment into the sensor die.

| Drive Signal | Shape |
| --- | --- |
| 726a | High frequency square wave |
| 726b | Low frequency square wave |
| 726c | High frequency sine wave |
| 726d | Low frequency sine wave |
| 726e | High frequency square wave with missing high pulse |
| 726f | Low frequency square wave with missing high pulse |
| 726g | High frequency sine wave with missing pulse |
| 726h | Low frequency sine wave with missing pulse |
| 726i | High frequency square wave with missing low pulse |
| 726j | Low frequency square wave with missing low pulse |

Referring again to FIG. 7, the fingerprint sensor 702 may be similar to fingerprint sensor 102 or fingerprint sensor 602. Controller 704, which includes drive signal blocks 722a-722j, generates drive signal 726a-726j, and injects them into fingerprint sensor 702. Fingerprint sensor 702 has ten drive signal injection points (not shown), and generates a fingerprint signal 752 corresponding to one of the drive signal 726a.

Each drive signal block 722 includes a fingerprint signal filter 756. Each fingerprint signal filter 756a-756j receives the corresponding drive signal 726a-726j and the fingerprint signal 752. Each fingerprint signal filter 756a-756j compares its respective drive signal 726a-726j with the fingerprint signal 752 and generates a match signal 758a-758h. Each match signal 758a-758j reflects the degree to which the fingerprint signal 752 corresponds to the respective drive signal 726a-726h. In this embodiment, each match signal 758 has a value between 0 and 255. The match signal 758 generated by each fingerprint signal filter 756 will have a value at or close to 0 if there is no or little correspondence between the respective drive signal 726 and the fingerprint signal 752. The match signal 758 will have a value at or close to 255 if there is high or exact correspondence between the respective drive signal 726 and the fingerprint signal 752. The fingerprint signal filter will typically, but not necessarily, be configured to take into account an appropriate time delay (which may be variable and automatically determined) between the generation of the drive signal 726 and the fingerprint signal 752. Each of the match signals 758 is transmitted to the processor 716. Typically, the fingerprint signal 752 will correspond to one of the drive signals 726 to a higher degree than the other drive signals.

Typically, a drive signal 726 will be coupled to sensor die 708 (not shown) when a finger is placed on the fingerprint sensor 702. Processor 716 utilizes the match signals 758 to determine the angular orientation of the finger. Processor 716 may be configured to do so in various ways. For example, in this embodiment, the processor 716 is configured to assume that the match signal having the largest magnitude corresponds to the angular orientation of the finger. In other embodiments, the processor may be configured to determine a weighted average of the match signal values and estimate an angular position based on the relative magnitudes of the match signals. In some embodiments, match signals having a valued below a threshold may be ignored in calculating the weighted average. This may be particularly relevant in embodiments where the drive signal injection points are positioned sufficiently closely that more than one drive signal injection point is coupled to the sensor die by a finger. The specific angular position of the finger may be estimated by calculated a weighted average of the match signal corresponding to the two or more drive signals reflected in the resulting fingerprint signal.

Figure 9:
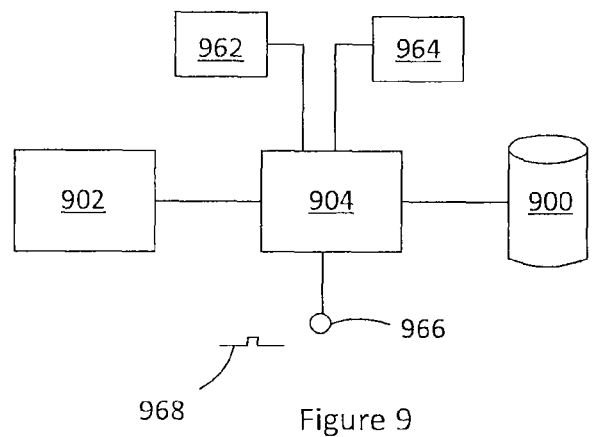
FIG. 9 is a block diagram illustrating an access control system.

Reference is next made to FIG. 9, which illustrates an access control system 900 for controlling access to an item such as an activity, system, location, facility, data or another item that a person may wish to access. System 900 includes a fingerprint sensor 902, a controller 904 and a fingerprint database 960, an input device 962 and an output device 964. Fingerprint sensor 902 and controller 904 may correspond to system 100, 600 or 700.

Controller 904 includes a processor 916, which is coupled to database 960. Processor 916 is also coupled to an authorization terminal 966 at which the processor 916 provides an authorization signal 968.

Fingerprint database 960 includes a plurality of authorized person records, wherein each authorized person record includes:

| Field | Contents |
| --- | --- |
| Authorized person identifier | An identifier for an authorized person |
| Angle A fingerprint | An image of the authorized person's finger rotated at angle A. |
| Angle B fingerprint | An image of the authorized person's finger rotated at angle B. |
| Angle C fingerprint | An image of the authorized person's finger rotated at angle C. |
| Angle D fingerprint | An image of the authorized person's finger rotated at angle D. |
| Angle E fingerprint | An image of the authorized person's finger rotated at angle E. |
| Angle F fingerprint | An image of the authorized person's finger rotated at angle F. |

| Field | Contents |
| --- | --- |
| Angle G fingerprint | An image of the authorized person's finger rotated at angle G. |
| Angle H fingerprint | An image of the authorized person's finger rotated at angle H. |
| Authorized angle sequence | A sequence of angular positions. |

The person record identifier field corresponds to a person. Each angle fingerprint field may record an image or other data corresponding to the person's fingerprint (typically of a specific finger such as the index finger) positioned on a fingerprint sensor. The authorized angle sequence is a sequence of angular finger positions.

Input device 962 may be a keyboard, keypad, mouse, touchscreen or other device that may be used by a person to provide input to processor 916. Output device 964 may be a display screen or other device that provides visual and/or audio output to a person using system 900.

Figure 10:
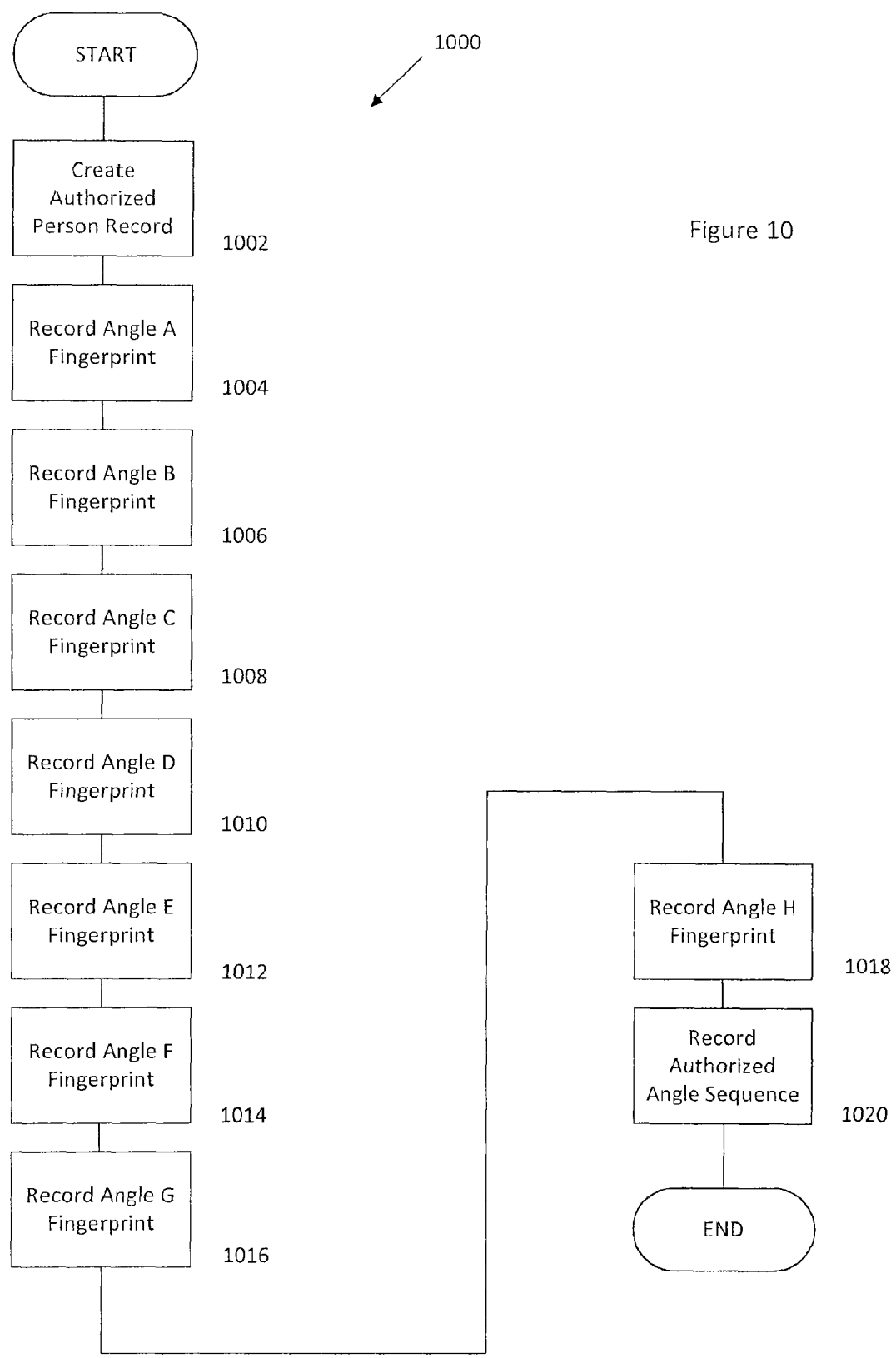
FIG. 10 is a flowchart illustrating a method of creating records in a fingerprint database.

Reference is next made to FIG. 10, which illustrates a method 1000 by which each record in the fingerprint database is populated. Method 1000 is performed under the control of processor 916, which may communicate with a person using the input device 962 and the output device 964.

Method 1000 begins in step 1002 in which an authorized person record is created for a person. An authorized person identifier is recorded for the person. In some embodiments, the authorized person identifier may be generated automatically by processor 916. In other embodiments, the person may enter an authorized person identifier using the input device 962. The authorized person identifier is recorded in the authorized person identifier field. The authorized person identifier for each person record in the fingerprint database is unique.

Method 1000 then proceeds to step 1004, in which the person positions his or her finger on the fingerprint sensor 902 with the tip of the finger at a 0° position (angle A). Processor 916 receives a fingerprint signal 952 and determines (i) the angular position of the person's finger and (ii) an image (or corresponding data) of the person's fingerprint. If the angular position corresponds to angle A, then the fingerprint image is recorded in the angle A fingerprint field. If the angular position does not correspond to angle A, then the person's fingerprint may be rescanned, or alternatively, method 1000 may end. When the person's fingerprint has been recorded in angle A, method 1000 proceeds from step 1004. In some embodiments, the person may be required to record fingerprint data for each angle A-H. In other embodiments, the person may be permitted to skip some or all of the angles A-H. If the person is permitted to skip angle A, and chooses to do so, method 1000 may proceed from step 1004.

Following step 1004, method 1000 proceeds to step 1006 (unless method 1000 was terminated during step 1004) in which the person's fingerprint is recorded with his or her finger positioned at angle B, the person is permitted to skip angle B or the method ends.

In this manner, method 1000 proceeds through steps 1004 to 1018 in which the person's fingerprint is recorded at angles A-H, or in at least some of the angles A-H.

Following step 1018, method 1000 proceeds to step 1020 in which the person is permitted to specify a sequence of fingerprint positions. For example, the person may specify the sequence ADHC. This sequence is recorded in the authorized angle sequence field.

Method 1000 then ends. A person who has a record in fingerprint database 960 may be referred to as an authorized person.

Method 1000 is repeated for a plurality of persons.

Figure 11:
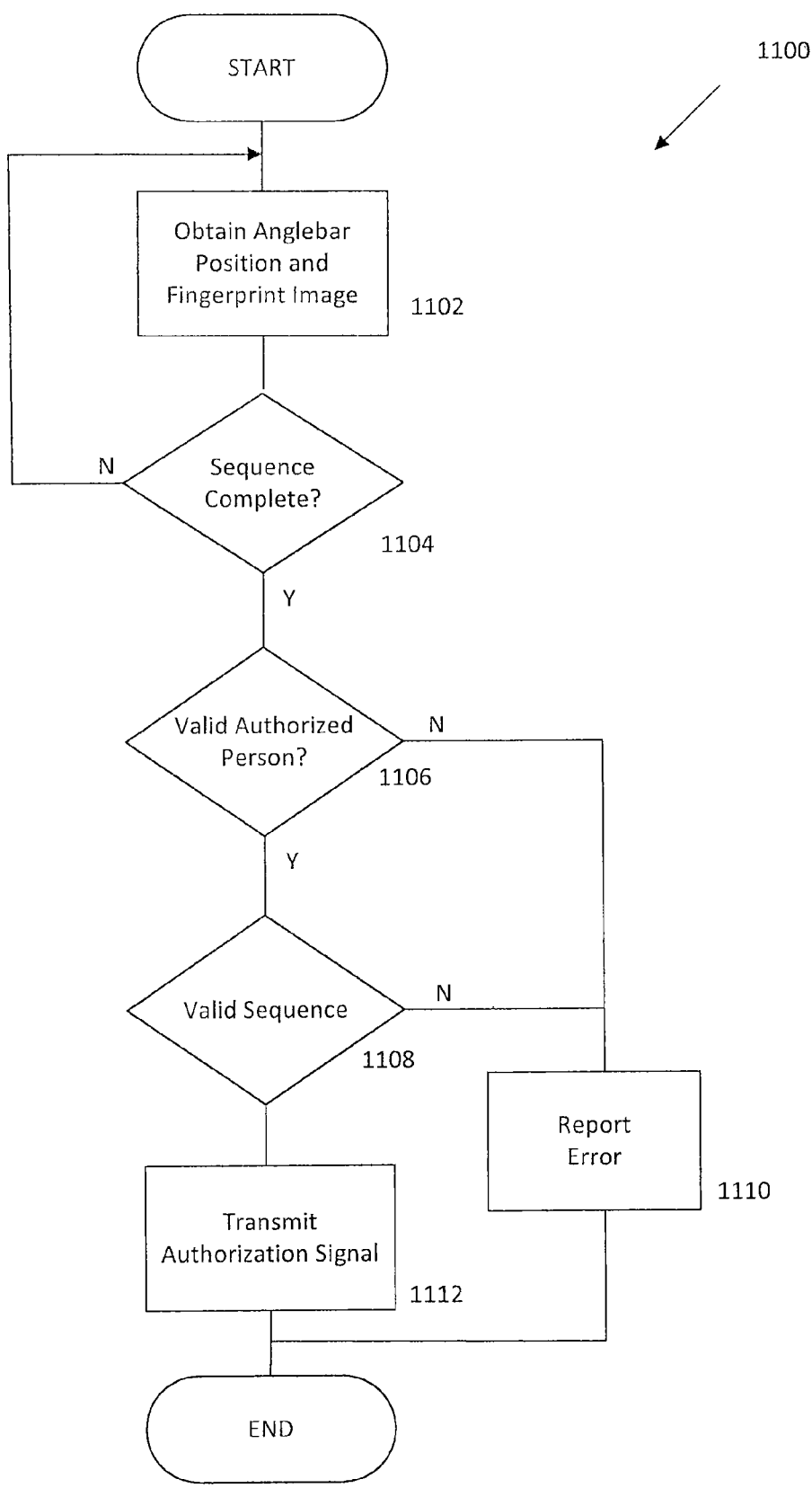
FIG. 11 is a flowchart illustrating a method of permitting an authorized person to access an item.

Reference is next made to FIG. 11, which illustrates a method 1100 by which system 900 may be used to permit an authorized person to access an activity or device, access data or for some other purpose.

Method 1100 begins in step 1102, in which the person positions his or her finger on fingerprint sensor 902. Processor 916 receives fingerprint signal 952 and determines (i) the angular position of the person's finger and (ii) a fingerprint image (or corresponding data) of the person's fingerprint. Processor 916 then compare fingerprint image to the fingerprint data recorded in the fingerprint database 960. If the fingerprint image corresponds to any recorded fingerprint, the processor then compares the angular position of the fingerprint image to the angular position of the corresponding recorded fingerprint. If the two angular positions match, then the processor records the angular position as the first angular position in a sequence of angular positions. The processor also records the authorized person identifier in the authorized person record in which the corresponding recorded fingerprint was found.

Method 1100 then proceeds to step 1104 in which the processor 916 determines if the sequence of angular positions is complete. If the sequence is complete, then method 1100 proceeds to step 1106. If the sequence of angular positions is not complete, then method 1100 returns to step 1102. In some embodiments, each authorized angle sequence recorded in the fingerprint database 960 may be of a predetermined length and step 1102 is repeated until the sequence of angular positions and corresponding authorized person identifiers has reached the predetermined length. In other embodiments, the person may indicate whether he or she wishes to add another angular position to the sequence. If so, method 1100 returns to step 1102. If the person indicates that the sequence is complete, then method 1100 continues to step 1106.

In step 1106, the processor 916 determines if the authorized person identifier recorded for each angular position in the recorded sequence is the same. If so, the authorized person identifier may be referred to as a candidate authorized person identifier and method 1100 continues to step 1108. Otherwise, method 1100 reports an error in step 1110 and ends. The error reported in step 1110 may indicate that the sequence has not been entered by an authorized person, that the sequence is invalid or may provide another message.

In step 1108, the processor 916 compares the sequence of angular positions recorded in iterations of step 1102 with the authorized angle sequence recorded in the authorized person record corresponding to the candidate authorized person identifier. If the sequence of angular positions matches the authorized angle sequence the candidate authorized person is authenticated as the authorized person corresponding to the authorized person record and method 1100 proceeds to step 1112. Otherwise, method 1100 proceeds to step 1110.

In step 1112, processor 916 transmits an authorization signal 968 indicating that the person should be permitted to access an activity, device, data or receive some other access corresponding to the candidate authorized person identifier.

For example, system 900 may be used to control access to an item such as a facility, a car wash, or data such as a bank account or other account. An authorized person must sequentially scan his or her finger using the fingerprint scanner 902 with the finger positioned in the correct angular positions, corresponding to the authorized angle sequence in the authorized person record for that person. If the person does so successfully, processor 916 transmits an authorization signal 968 allowing the authorized person to access the facility, activity, data or other item that is protected by the system 900.

In system 900, the authorized person is not required to identify him or herself prior to scanning his or her finger for the first time in step 1102. The person's identity is assumed to correspond to the authorized person identifier that corresponds to each fingerprint scan. (If each fingerprint scan does not correspond to the same authorized person record and to the same authorized person identifier, then method 1100 exits following step 1106.) Such a system may be used to allow access when the item being accessed is not specific to the authorized person, but is secured to prevent unauthorized persons from accessing it. System 900 may also be used to control access to an item that is specific to the authorized person, such as access to a bank account at an automated teller machine (ATM). In such an embodiment, a person who is authenticated as an authorized person using method 1100 is given access to an account corresponding to the authorized person identifier corresponding to each fingerprint scan in step 1102.

In other embodiments, a person may be required to identify him or herself prior to step 1102. For example, the person may be required to enter in an authorized person identifier or other data that can be correlated by processor 916 to an authorized person identifier. In some embodiments, the authorized person may identify himself by presenting an identification card, tag (such as an RFID tag), bar code or other identification code or device to an appropriate scanner. Typically, the scanner will be located with the fingerprint scanner 902 and coupled to the controller 904 to allow the authorized person record corresponding to the identification code or device to be identified and accessed. Each fingerprint scan made in step 1102 must correspond to fingerprint data recorded in the corresponding authorized person record in order for the person to receive access.

In system 900, the fingerprint database 960 is accessible to controller 904. In other embodiments, it may be desirable to allow the fingerprint database to be accessed from a plurality of locations and systems.

Figure 12:
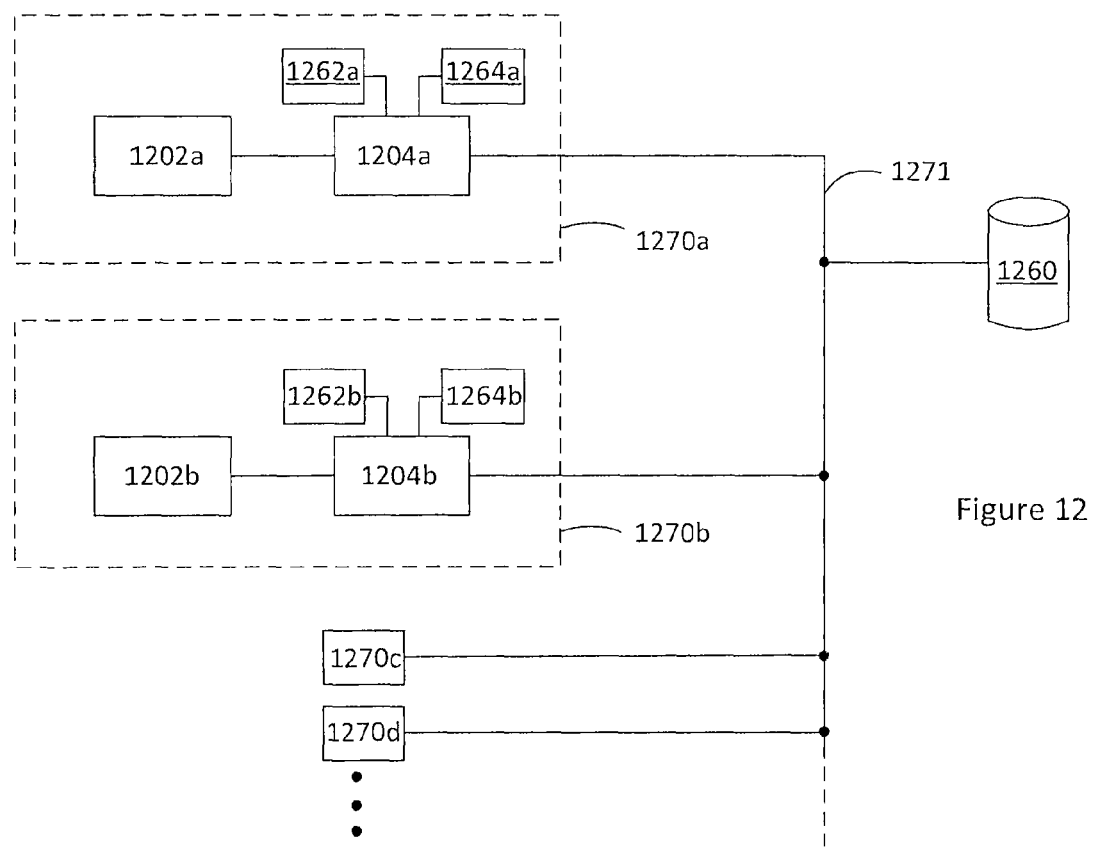
FIG. 12 is a block diagram illustrating another access control system.

Reference is next made to FIG. 12, which illustrates another access control system 1200. Access control system 1200 is similar to access control system 900 and similar components are identified by corresponding reference numerals. Access control system 1200 includes a plurality of access control modules 1270, each of which comprises a fingerprint scanner 1202, a controller 1204, an input device 962 and an output device 964. Each controller 1204 is coupled to a fingerprint database 1260 through a communication network 1271. Fingerprint database 1260 may be located at a central location while some or all of the access control modules are located remotely from the fingerprint database 1260. Communication network 1271 may be any type of communication network. In some embodiments, one or more access control modules 1270 may be coupled directly to the fingerprint database.

Access control system 1200 may be used to control access for a plurality of authorized users to a system from a plurality of locations. For example, system 1200 may be used to control access to ATMs. A bank may integrate an access control module 1270 into some or all of its ATMs. A customer of the bank may register for ATM access to the customer's bank accounts by attending at a bank location and using an access control module 1270 at the bank location to create an authorized person record in the fingerprint database 1260 in accordance with method 1000 (FIG. 10). Subsequently, the person may authenticate himself or herself at an ATM using method 1100 (FIG. 11). When the customer successfully completes method 1100, the customer is permitted to access banking activities at the ATM. In some embodiments, the processor (not shown) in the controller 1204 may also control other operations at the ATM. In other embodiments, the controller 1204 may generate an authorization signal that is coupled to a controller for other ATM functions. The authorization signal may indicate the identity of the authorized customer, allowing the customers accounts to be given access to his or her own accounts.

In system 900, the fingerprint database 960 includes fingerprint images or corresponding data for a plurality of angular positions for each authorized person. In some embodiments, the fingerprint database may include only a single fingerprint image or corresponding data for each authorized person.

Figure 13:
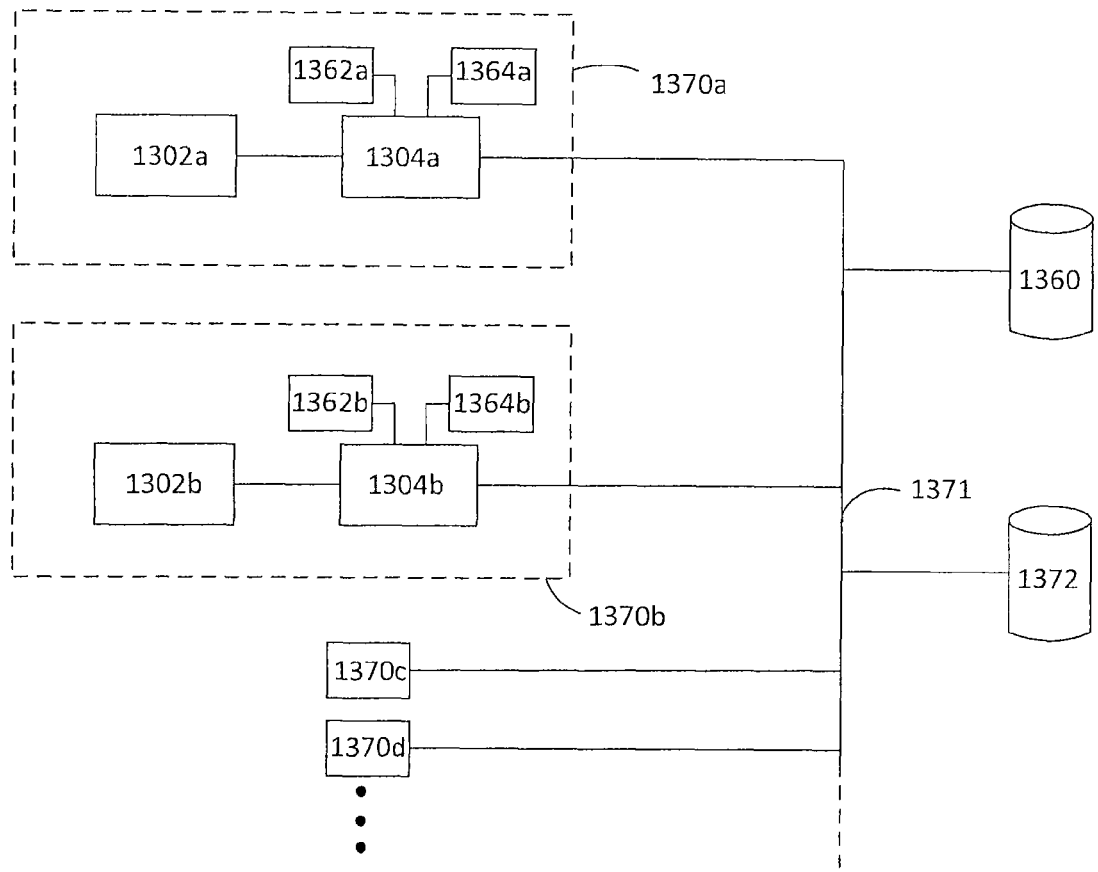
FIG. 13 is a block diagram illustrating another access control system.

Reference is next made to FIG. 13, which illustrates another access control system 1300. System 1300 has a plurality of access control modules 1370, a fingerprint database 1360 and an authorization sequence database 1372.

Fingerprint database 1360 includes a plurality of fingerprint records, each of which includes:

| Field | Contents |
| --- | --- |
| Authorized person identifier | An identifier for an authorized person |
| Fingerprint data | An image of the authorized person's finger or corresponding data. |

Authorization sequence database 1372 includes a plurality of sequence records, each of which includes:

| Field | Contents |
| --- | --- |
| Authorized person identifier | An identifier for an authorized person |
| Authorized angle sequence | A sequence of angular positions |

System 1300 may be used to control access to an item, like systems 900 and 1200. For each authorized person, a fingerprint record is recorded in the fingerprint database 1360 and a sequence record is recorded in the authorization sequence database 1372.

To authenticate or identify a person as an authorized person, the processor in an access control module 1370 obtains a sequence of fingerprint signals and assembles a sequence of angular positions and corresponding fingerprint images (similar to step 1102 and 1104 of method 1100 (FIG. 11)). The processor accesses the fingerprint database 1360 to determine if each fingerprint image corresponds to the same authorized person. If not, the person is not authenticated as an authorized person (similar to step 1106). The processor accesses the authorization sequence database 1372 to determine if the sequence of angular positions corresponds to the authorized angle sequence recorded for the same authorized person. If so, the person is authenticated as the authorized person identified by the matching authorized person identifiers in the fingerprint database 1360 and the authorization sequence database 1372.

The fingerprint database 1360 of system 1300 may be a fingerprint database maintained by a third party. For example, an individual may register his or her fingerprint in fingerprint database 1360. Subsequently, the individual may register with to access an item secured with system 1300. The individual may then record an authorized angle sequence in authorized sequence database 1372, which may be maintained by the operator of system 1300 or by a third party.

In other embodiments, a system may include more than one fingerprint database may be incorporated into a system, allowing individuals who have registered their fingerprints with various fingerprint databases to use the system.

Some fingerprint databases do not include angular information for fingerprint data. In such systems, if a fingerprint is scanned at any angle, it may be matched to a corresponding fingerprint that was originally scanned at a different angle. System 1300 may be used with such systems. By determining the angular placement of a finger when a fingerprint is scanned and independently verifying a fingerprint match, system 1300 allows an existing fingerprint database to be used with the additional security offered by angular authorization sequences.

In the system described above, each authorized person records one or more fingerprints for a single finger. In other embodiments, the person may record one or more fingerprints for more than one finger, allowing authorization sequences to incorporate both sequences of different fingers and different angular positions for each finger in the sequence.

In some embodiments, an authorized sequence may include a sequence of different fingers, without requiring specific angular placement.

In some embodiments, it may be desirable to allow access only if two or more persons are authenticated. In some embodiments, the person may be authenticated independently. In other embodiments, an authorized sequence may include fingerprints from each of the persons, requiring them to cooperate to scan their fingers in an authorized sequence.

In the embodiments described above, one authorized angle sequence is recorded for each authorized person. In other embodiments, two or more authorized angle sequences may be recorded for some or all of the authorized persons. Each authorized sequence may be used to allow access to the same item, or some authorized angle sequences may be used to trigger access to different items. For example, an authorized person may use different authorized angle sequences to obtain access to different parts of a facility. In some embodiments, some angle sequences may trigger specific functions. For example, a bank customer may have use one authorized angle sequence to obtain access to the person's bank accounts at an ATM under normal conditions, but may use a different authorized angle sequence if the customer is being forced to access his or her accounts under duress. The second authorized angle sequence may trigger an emergency response, reduced balances being displayed for the customer's accounts, a reduced withdrawal limit being provided or a combination of these and other actions.

In some embodiments, a series of single use authorized angle sequences may be generated for an authorized person. The series of single use authorized angle sequences are recorded in an authorized sequence database and is also provided to the authorized person. Each time that the authorized person uses an access control system to access an item, the authorized person must use a different single authorized angle sequence. Once an authorized angle sequence has been used, it is no longer valid.

The access control systems described above combine several security features to authenticate a person as an authorized person. A person is authenticated if the person enters the correct biometric fingerprint data as well as entering a correct sequence or code. Thus an unauthorized person who coincidentally has a fingerprint matching that of an authorized person is unlikely to be authenticated because the unauthorized person will likely not know the authorization sequence for the authorized person. An unauthorized person who knows the correct authorization sequence is unlikely to be authenticated because the unauthorized person is unlikely to have the necessary fingerprint. By combining biometric and code based security concepts, the access control systems are more secure than systems that use only one security technique.

Figure 15A:
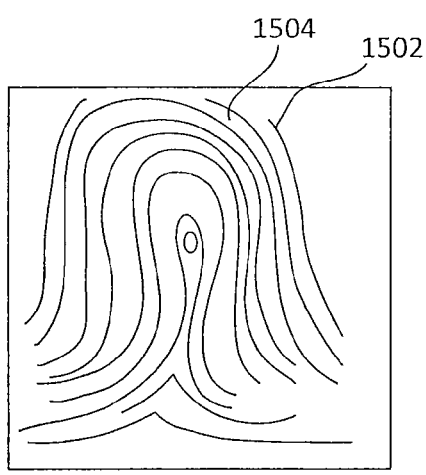
FIGS. 15a and 15b illustrate a fingerprint in various conditions during a person's heartbeat.
Figure 15B:
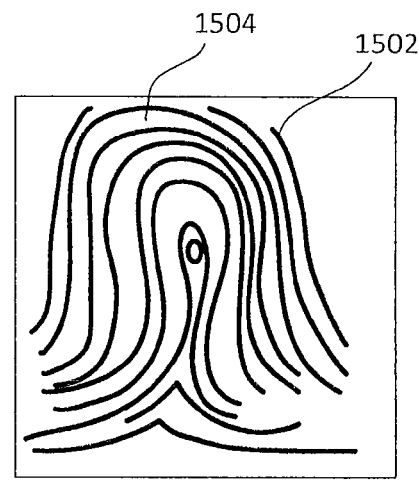

Reference is next made to FIGS. 15*a* and 15*b*. The systems described above describe the use of a conductive finger to couple a drive signal from a bezel or bezel segment to a sensor die. In some cases, a finger that has been removed from a person will sufficiently couple a drive signal to allow the severed finger to be used to authenticate a person. Typically, a person's heart beat causes fluctuations in the skin surface, including the fingertips, which results in a rhythmic variation in the pressure between a finger and the sensor die. FIG. 15*a* illustrates a fingerprint image obtained when a finger is pressed against a sensor die with less pressure. FIG. 15*b* illustrates a fingerprint image obtained when the finger is pressed against a sensor die with greater pressure. In some embodiments, the processor may examine some or all of a fingerprint image to determine if the width of lines 1502 is expanding and contracting within the heartbeat frequency a typical heart rate, and if not, then the processor may be configured to refuse to authenticate a person. In this manner, the processor may be able to refuse authentication if a severed finger is used.

Figure 16A:
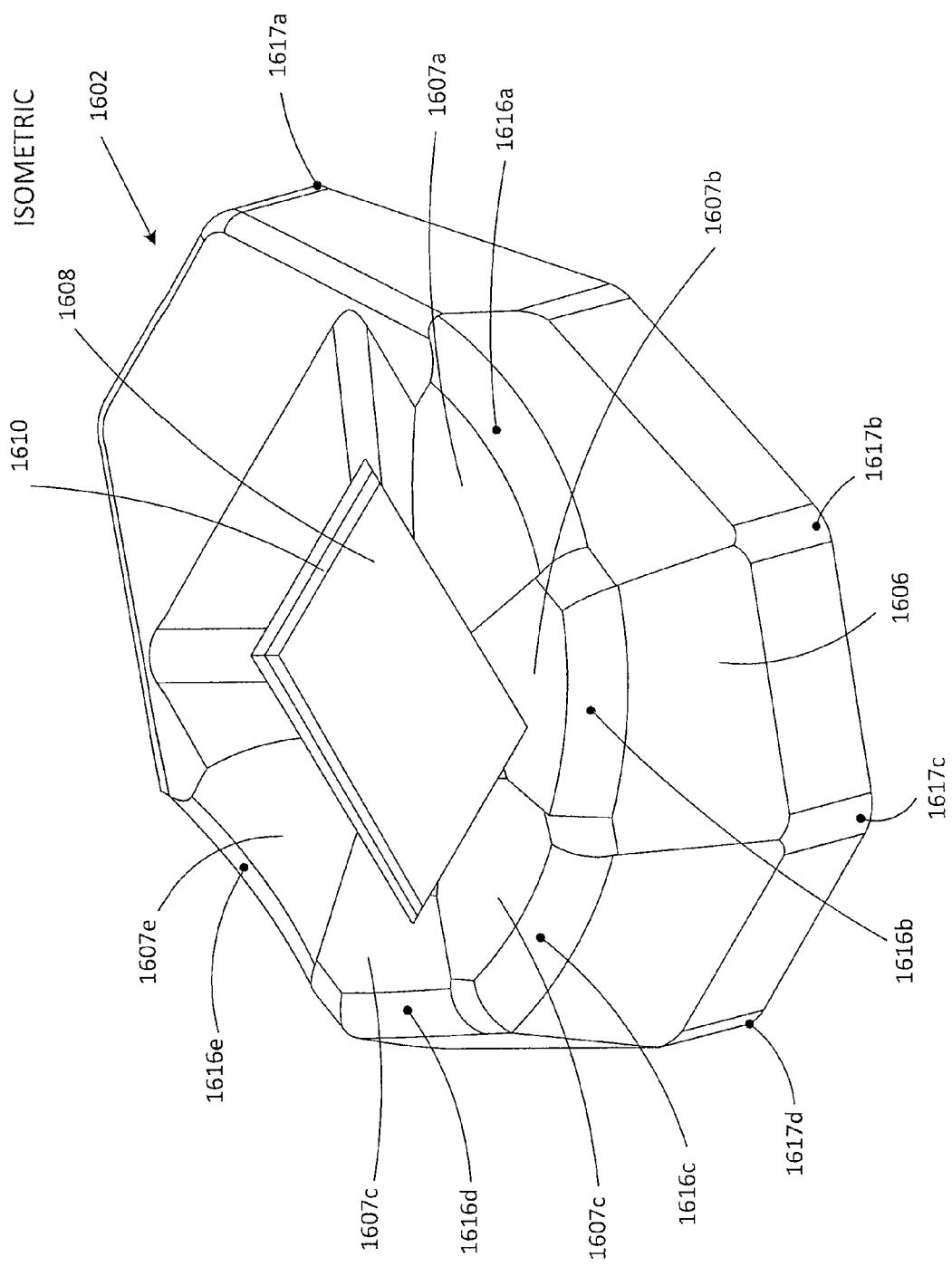
FIG. 16a-16c are, respectively, isometric, top and side views of a fingerprint sensor.
Figure 16B:
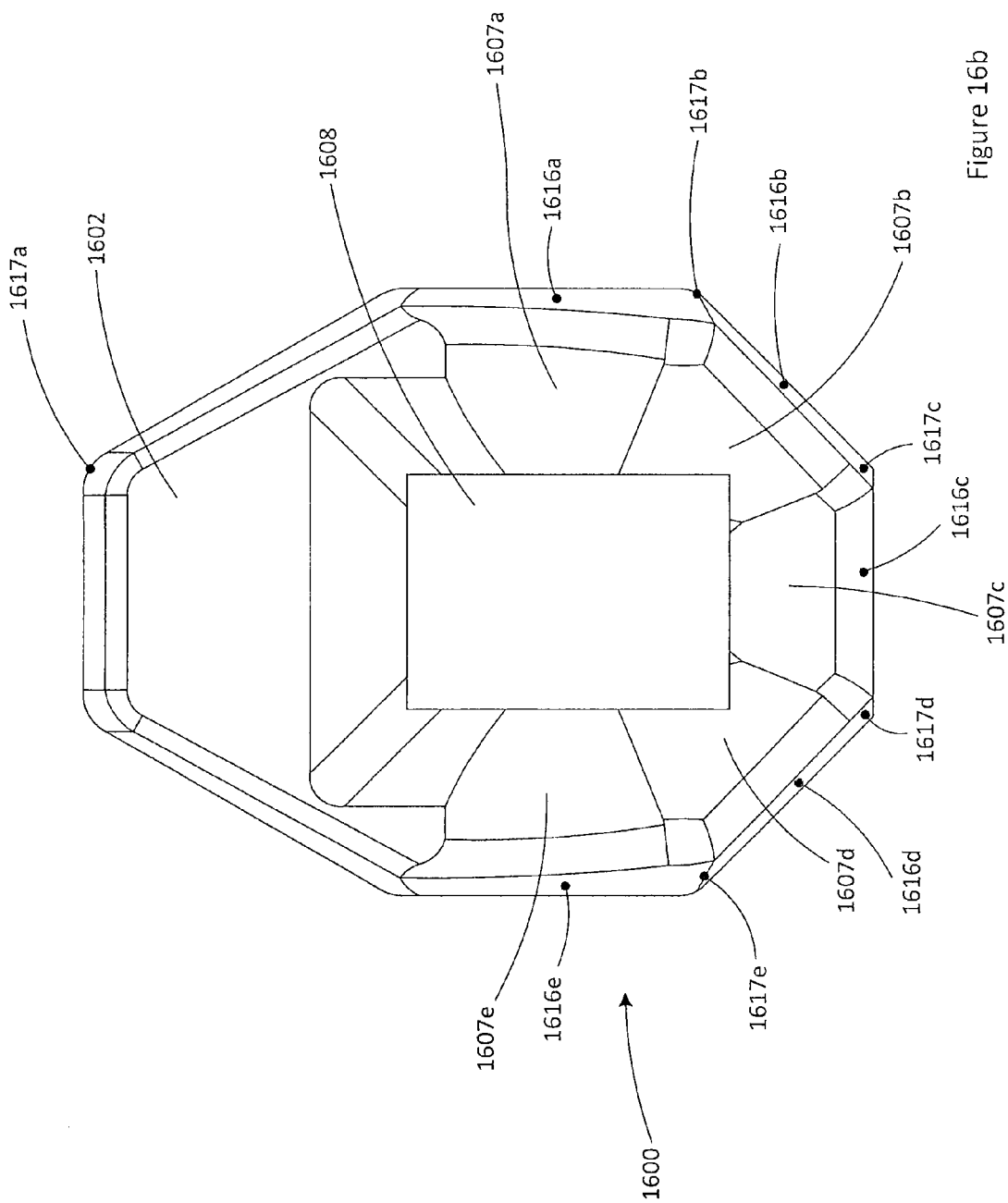
Figure 16C:
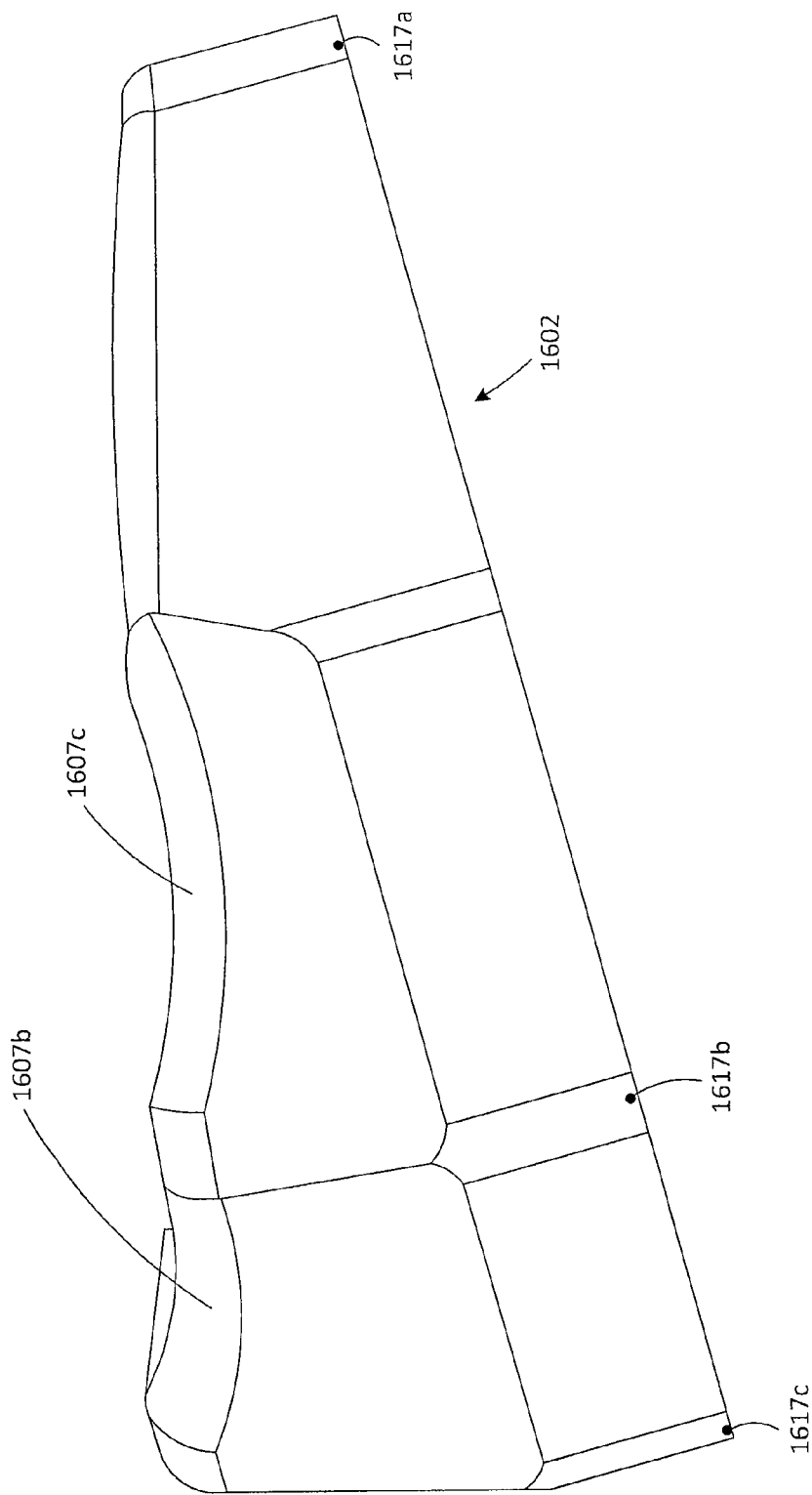

Reference is next made to FIG. 16*a*-16*c*, which illustrate a fingerprint sensor 1602. Finger print sensor 1602 has continuous bezel 1606 that, in some embodiments, is made of a metal. Five finger guides 1607*a*-1607*e* are formed in the bezel to guide a user in properly positioning his or her finger in one of five angular positions, illustrated in FIG. 16*b* as the −90°, −45°, 0°, 45° and 90° positions. A drive signal injection point 1616*a*-1616*e* is positioned in each finger guide 1607*a*-1607*e*. Optional ground points 1617*a*-1617*e* are positioned between the finger guides 1607. Fingerprint sensor 1602 has a sensor die 1608 that is insulated from the bezel 1608 by an insulator 1610.

Fingerprint sensor 1602 is suitable for use with embodiments according to systems 100 and 700 and the various access control systems described above.

In some embodiments, it may be desirable to reduce power consumption. Reference is next made to FIGS. 17*a*, 17*b* and 17*c*, which illustrate several fingerprint sensors that include user presence detection systems. When a system is not use, the system may enter a low power mode in which the user presence detection system is active, but other functions are not active to reduce power consumption. Reduced power consumption may be particularly desirable in systems that are battery powered, or powered by low power supplies such as USB ports. When a user is detected, the system is activated.

Figure 17:
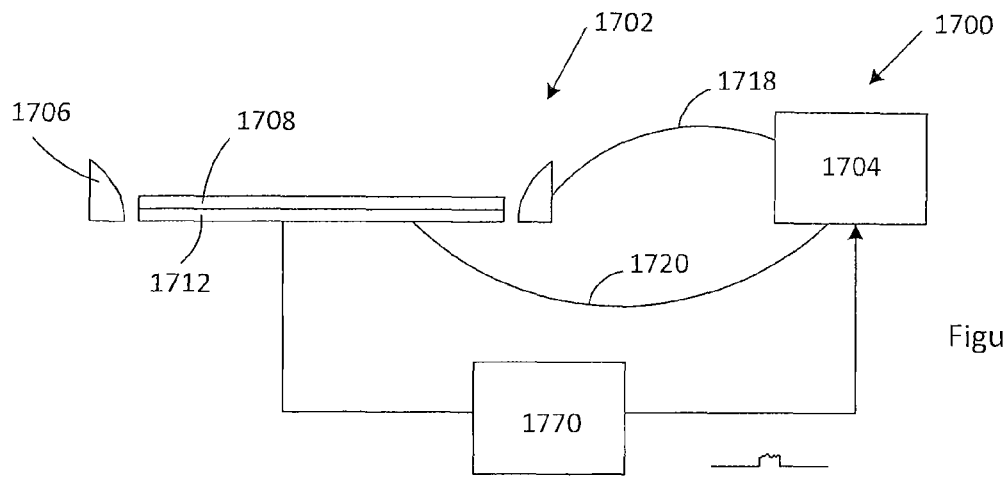
FIGS. 17-19 illustrate several low-power fingerprint sensing systems.

FIG. 17 illustrates a fingerprint sensing system 1700. Components of system 1700 that correspond to the embodiments described above are identified by similar reference numerals. Finger print sensor 1702 and controller 1704 are coupled together through communication links 1718 and 1720. System 1700 includes an activity sensing sub-system comprising a high gain block 1770. Die connection layer 1712 is coupled to controller 1704 through a high gain block 1770.

In operation, when system 1700 is not in use (i.e. has not been used for some time period), controller 1704 puts system 1700 into a low power mode. In the low power mode, the controller 1704 may stop generating and injecting drive signals, may stop acquiring and analyzing fingerprint signals and may take other steps to reduce power consumption. When a person touches sensor die 1718, the person will typically couple a relatively small signal into the sensor die. The small signal will typically correspond to electrostatic and electromagnetic noise surrounding the person, such as power line signals, static charges, etc. The coupled signal is amplified by the high gain block 1770, which generates a "wake-up" signal 1780. In response to the wake-up signal 1780, processor 1704 activates system 1700 into a normal operation mode and begins operating system 1700 as described above. During normal operation, controller 1704 may turn off high gain block 1770 to reduce power consumption.

Figure 18:
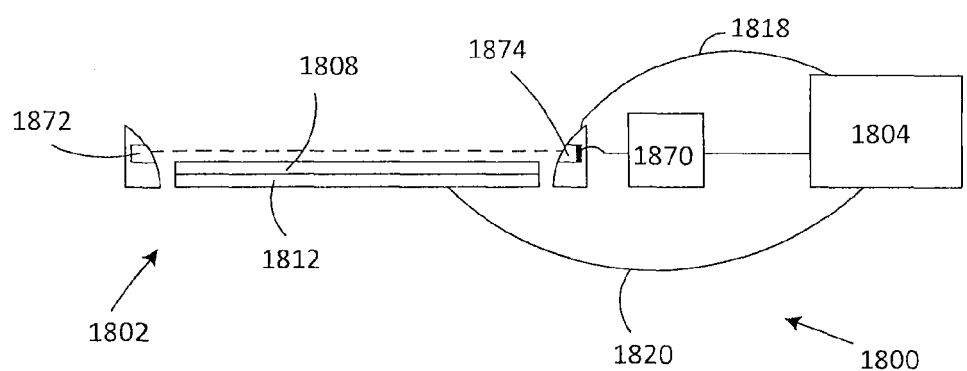

FIG. 18 illustrates another fingerprint sensing system 1800. Components of system 1800 that correspond to embodiments described above are identified by similar reference numerals. System 1800 includes an activity sensing subsystem, which comprises an optical transmitter 1872, an optical receiver 1874 and high gain block 1870. Like system 1700, system 1800 operates in a low power mode when the system is inactive. In the low power mode, optical transmitter 1872 (which may be a low power LED or IR source) transmits light above the sensor die 1808. The light is detected by the optical receiver 1874. If the beam of light is broken (typically be a finger being placed on the sensor die), and thus light is not received at optical receiver 1874, high gain block 1870 generates a wake-up signal 1880 and controller 1804 returns system 1800 to its normal operation mode. Optionally, the light signal transmitted by optical transmitter 1872 may be pulsed to reduce power, and optical receiver 1874 synchronously detects the transmitted light.

Figure 19:
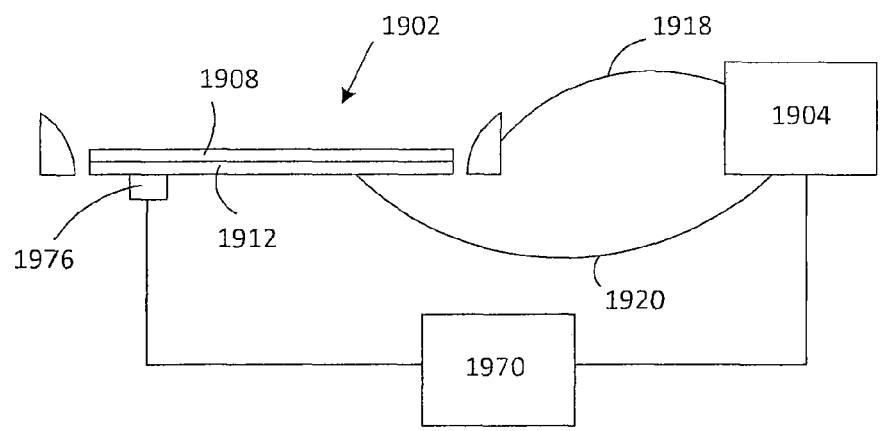

Reference is next made to FIG. 19, which illustrates another fingerprint sensing system 1900. Components of system 1900 that correspond to embodiments described above are identified by similar reference numerals. System 1900 includes an activity sensing block that includes an accelerometer or vibration sensor 1976 and a high gain block 1970. System 1900 has a low power mode in which high gain block 1970 monitors accelerometer 1976. Accelerometer 1976 is response to movement of the fingerprint sensor 1902 and generates a movement signal 1982 corresponding to the movement of the fingerprint sensor. If the movement signal 1982 indicates movement beyond a threshold, then high gain block 1970 generates a wakeup signal 1980, in response to which the controller 1904 returns system 1900 to it normal operation mode. By selecting the threshold, system 1900 can be configured to wake up and return to its normal operation mode in response to a small vibration, repeated tapping on the sensor die by a finger or another vibration level.

The fingerprint sensing systems and access control systems may be combined with other security or authorization systems to control access to an item. For example, in an ATM system, an access control system as described above may be combined with a magnetic stripe or other scanner to allow bank customers to use either or both of a fingerprint based access control system or a traditional bank card/passcode authentication system.

In a time and attendance system used to track the presence of employees at their places of employment (or other system requiring proof that a person has attended a location), an access control system may be used to track employees or other person upon entering and exiting a facility. In some cases, one of the person's fingers (the index finger for example) may be used when entering the facility. A second finger (the middle finger) may be used when leaving the facility. A third finger may be used to indicated distress or call for help, such as in a case where an unauthorized person is forcing an employee to give the unauthorized person access to the facility.

An access control system may also be used to provide access to hotel rooms and other locations, in place of or in combination with magnetic or RFID based cards or keys. A user may scan in a fingerprint and record an access sequence when registering at the hotel. The user may then repeat the access sequence at a fingerprint scanner at a room door to access the room.

The present invention has been described here by way of example only. Various modification and variations may be made to these exemplary embodiments without departing from the spirit and scope of the invention.

We claim:

1. A method of operating an access control system, the method comprising:
    recording fingerprint data corresponding to one or more fingers of a particular authorized person;
    recording a plurality of sequences of finger positions for the particular authorized person;
    associating each sequence of finger positions with a corresponding response signal;
    providing a fingerprint sensor having a sensor die and a bezel, wherein the bezel has a plurality of drive signal injection points;
    injecting a drive signal into each of the drive signal injection points wherein each drive signal has a unique shape distinguishable from the other drive signals;
    receiving a series of fingerprint signals from the fingerprint sensor, wherein each fingerprint signal corresponds to at least one of the drive signals;
    determining a sequence of angular positions corresponding to sequential fingerprint signals in the series by determining the at least one drive signal to which each received fingerprint signal corresponds;
    determining if each of the fingerprint signals corresponds to the recorded fingerprint data;
    determining if the sequence of angular positions corresponds to a particular sequence of finger positions in the recorded plurality of sequences of finger positions; and
    if the fingerprint signals correspond to the recorded fingerprint data and the sequence of angular positions corresponds to the particular sequence of fingerprint positions, then providing the corresponding response signal associated with that particular sequence of finger positions.

2. The method of claim 1 wherein at least one of the corresponding response signals is an authorization signal that includes an identification of the authorized person.

3. The method of claim 2, further comprising:
    identifying variations in the received fingerprint signals;
    determining if the variations correspond to a typical heart rate; and
    providing the authorization signal if and only if the identified variations correspond to the typical heart rate.

4. The method of claim 1 wherein each sequence of finger positions is specified by the authorized person.

5. The method of claim 1 wherein the fingerprint data corresponds to one or more fingers of the authorized person positioned in multiple angular positions on a fingerprint sensor.

6. The method of claim 1 wherein the fingerprint data corresponds to one or more fingerprints of the authorized person in a standard orientation.

7. The method of claim 1 wherein the fingerprint data and each sequence of finger positions of the particular authorized person are recorded in an authorized person record in a fingerprint database that contains authorized person records for a plurality of authorized persons.

8. The method of claim 7 including requiring the particular authorized person to identify himself or herself prior to providing the corresponding response signal.

9. The method of claim 1, wherein:
recording fingerprint data corresponding to one or more fingers of the particular authorized person comprises recording fingerprint data corresponding to at least two fingers of the particular authorized person, the at least two fingers including a first finger and a second finger; and
at least one sequence of finger positions includes a first finger position associated with the first finger of the particular authorized person and a second finger position associated with the second finger of the particular authorized person.

10. The method of claim 1, wherein:
recording fingerprint data corresponding to one or more fingers of the particular authorized person comprises recording fingerprint data corresponding to at least two fingers of the particular authorized person, the at least two fingers including a first finger and a second finger;
a first sequence of finger positions includes a particular finger position associated with the first finger of the particular authorized person; and
a second sequence of finger positions includes the particular finger position associated with the second finger of the particular authorized person.

11. The method of claim 10, wherein:
the first sequence of finger positions includes a particular sequence of finger positions with each finger position in the particular sequence of finger positions associated with the first finger of the particular authorized person; and
the second sequence of finger positions includes the particular sequence of finger positions with each finger position in the particular sequence of finger positions associated with the second finger of the particular authorized person.

12. The method of claim 1, wherein at least one of the corresponding response signals is a distress response signal.

13. The method of claim 1, wherein the drive signals injected into each drive signal injection point have temporally distinct active and inactive phases.

14. A method of operating an access control system, the method comprising:
providing a fingerprint sensor having a sensor die and a bezel, wherein the bezel has a plurality of drive signal injection points, each drive signal injection point being associated with an angle on the fingerprint sensor;
injecting a drive signal into each of the drive signal infection points, wherein each drive signal has a unique shape distinguishable from the other drive signals;
recording fingerprint data corresponding to one or more fingers of a particular authorized person rotated at a variety of angles on the fingerprint sensor;
recording a plurality of sequences of angular finger positions for the particular authorized person;
associating each sequence of finger positions with a corresponding response signal;
receiving a series of fingerprint signals from the fingerprint sensor, wherein each fingerprint signal corresponds to at least one of the drive signals;
determining if the received series of fingerprint signals corresponds to the particular sequence of angular finger positions by determining the at least one drive signal to which each received fingerprint signal corresponds; and
if each of the fingerprint signals corresponds to the recorded fingerprint data and to a particular sequence of finger positions in the recorded plurality of sequences of angular finger positions, then providing the corresponding response signal associated with that particular sequence of finger positions.

15. The method of claim 14 wherein at least one of the corresponding response signals is an authorization signal that includes an identification of the particular authorized person.

16. The method of claim 15, further comprising:
identifying variations in the received fingerprint signals;
determining if the variations correspond to a typical heart rate; and
providing the authorization signal if and only if the identified variations correspond to the typical heart rate.

17. The method of claim 14 wherein each sequence of finger positions is specified by the particular authorized person.

18. The method of claim 14 wherein the fingerprint data and each sequence of finger positions of the particular authorized person are recorded in an authorized person record in a fingerprint database that contains authorized person records for a plurality of authorized persons.

19. The method of claim 18 including requiring the particular authorized person to identify himself or herself prior to providing the corresponding response signal.

20. The method of claim 14, wherein:
recording fingerprint data corresponding to one or more fingers of the particular authorized person comprises recording fingerprint data corresponding to at least two fingers of the particular authorized person, the at least two fingers including a first finger and a second finger; and
at least one sequence of angular finger positions includes a first angular finger position associated with the first finger of the particular authorized person and a second angular finger position associated with the second finger of the particular authorized person.

21. The method of claim 14, wherein:
recording fingerprint data corresponding to one or more fingers of the particular authorized person comprises recording fingerprint data corresponding to at least two fingers of the particular authorized person, the at least two fingers including a first finger and a second finger;
a first sequence of angular finger positions includes a particular angular finger position associated with the first finger of the particular authorized person; and
a second sequence of angular finger positions includes the particular angular finger position associated with the second finger of the particular authorized person.

22. The method of claim 21, wherein:
the first sequence of angular finger positions comprises a particular sequence of angular finger positions with each angular finger position in the particular sequence of angular finger positions associated with the first finger of the particular authorized person; and
the second sequence of angular finger positions comprises the particular sequence of angular finger positions with each angular finger position in the particular sequence of angular finger positions associated with the second finger of the particular authorized person.

23. The method of claim 14, wherein at least one of the corresponding response signals is a distress signal.

24. The method of claim 14, wherein the drive signals injected into each drive signal injection point have temporally distinct active and inactive phases.

25. An access control system comprising:
a fingerprint sensor, wherein the fingerprint sensor has a sensor die and a bezel, the bezel has a plurality of signal injection points, and each signal injection point is associated with an angular position on the fingerprint sensor;
a controller coupled to the fingerprint sensor, wherein the controller includes a plurality of drive signal blocks, wherein each drive signal block is coupled to a corresponding signal injection point to inject a drive signal into the corresponding signal injection point and each drive signal block injects a drive signal having a unique shape distinguishable from the drive signal injected by every other drive signal block;
a fingerprint database coupled to the controller, wherein the fingerprint database includes a plurality of authorized person records, each of the authorized person records containing fingerprint data corresponding to an authorized person and a plurality of angle sequences, each angle sequence associated with a corresponding response, the plurality of angle sequences including an authorized angle sequence associated with an authorization response; and
wherein the controller is configured to receive a series of fingerprint signals from the fingerprint sensor, and determine if the received series of fingerprint signals corresponds to one of the angle sequences by determining the at least one drive signal to which each received fingerprint signal corresponds.

26. The system of claim 25, wherein the fingerprint data includes data corresponding to one or more of the particular authorized person's fingerprints positioned at a plurality of angular positions on the fingerprint sensor.

27. The method of claim 26, wherein:
a particular authorized person record contains fingerprint data corresponding to at least two fingers of the particular authorized person's fingerprints, the at least two fingers including a first finger and a second finger; and
the particular authorized person record contains at least one angle sequence having a first angular position associated with the first finger of the particular authorized person and a second angular position associated with the second finger of the particular authorized person.

28. The system of claim 26, wherein:
a particular authorized person record contains fingerprint data corresponding to at least two fingers of the particular authorized person's fingerprints, the at least two fingers including a first finger and a second finger;
the particular authorized person record contains a first angle sequence having a particular angular position associated with the first finger of the particular authorized person, and a second angle sequence having the particular angular position associated with the second finger of the particular authorized person.

29. The system of claim 28, wherein:
the first angle sequence has a particular angle sequence of angular positions with each angular position in the particular sequence of angular positions associated with the first finger of the particular authorized person; and
the second angle sequence has the particular angle sequence of angular positions with each angular position in the particular sequence of angular positions associated with the second finger of the particular authorized person.

30. The system of claim 25, wherein the controller is configured to:
identify variations in fingerprint signals received from the fingerprint sensor;
determine if the variations correspond to a typical heart rate; and
provide the authorization response if and only if the identified variations correspond to the typical heart rate.

31. The system of claim 25, wherein the plurality of angle sequences includes a distress angle sequence associated with a distress response.

32. The system of claim 25, wherein each drive signal block injects a drive signal with active and inactive phases distinct from the drive signal injected by every other drive signal block.

33. An access control system comprising
a fingerprint sensor having a sensor die and a bezel, the bezel having a plurality of signal injection points, and each signal injection point being associated with an angular position on the fingerprint sensor;
a controller coupled to the fingerprint sensor, the controller including a plurality of drive signal blocks, each drive signal block coupled to a corresponding signal injection point to inject a drive signal into the corresponding signal injection point and each drive signal block injects a drive signal having a unique shape distinguishable from the drive signal injected by every other drive signal block; and
a fingerprint database coupled to the controller, wherein the fingerprint database includes an authorized person record containing fingerprint data corresponding to at least one finger of an authorized person and a plurality of sequences of finger positions for the authorized person, each sequence of finger positions associated with a corresponding response;
wherein the controller is configured to receive a series of fingerprint signals from the fingerprint sensor, determine if each of the fingerprint signals corresponds to the fingerprint data in the authorized person record, determine if the series of fingerprint signals corresponds to a particular sequence of finger positions for the authorized person by determining the at least one drive signal to which each received fingerprint signal corresponds, and provide the corresponding response associated with that particular sequence of finger positions if the received series of fingerprint signals correspond to the fingerprint data and the particular sequence of finger positions.

* * * * *